United States Patent
Cauley, III

(10) Patent No.: US 10,046,322 B1
(45) Date of Patent: Aug. 14, 2018

(54) REACTION WELL FOR ASSAY DEVICE

(71) Applicant: Talis Biomedical Corporation, Menlo Park, CA (US)

(72) Inventor: Thomas H. Cauley, III, Redwood City, CA (US)

(73) Assignee: TALIS BIOMEDICAL CORPORATION, Menlo Park, CA (US)

( * ) Notice: Subject to any disclaimer, the term of this patent is extended or adjusted under 35 U.S.C. 154(b) by 0 days.

(21) Appl. No.: 15/928,551

(22) Filed: Mar. 22, 2018

(51) Int. Cl.
| | |
|---|---|
| *B01L 3/00* | (2006.01) |
| *G01N 1/00* | (2006.01) |
| *G01N 1/10* | (2006.01) |
| *B01J 19/00* | (2006.01) |

(52) U.S. Cl.
CPC ....... *B01L 3/502769* (2013.01); *B01L 3/5027* (2013.01); *G01N 1/10* (2013.01); *B01J 19/0046* (2013.01); *B01J 2219/00585* (2013.01); *B01J 2219/00596* (2013.01); *B01L 3/502715* (2013.01); *B01L 3/502723* (2013.01); *B01L 2200/028* (2013.01); *B01L 2200/0621* (2013.01); *B01L 2200/14* (2013.01); *B01L 2200/16* (2013.01); *B01L 2300/0816* (2013.01); *B01L 2300/0819* (2013.01); *B01L 2300/0861* (2013.01); *B01L 2400/043* (2013.01)

(58) Field of Classification Search
CPC ....... B01L 3/502769; B01L 2300/0816; B01L 2300/0819; B01L 2300/0861; B01L 3/5027; B01L 3/502723; B01L 2200/028; B01J 19/0046; B01J 2219/00585; B01J 2219/00596; G01N 1/10
See application file for complete search history.

(56) References Cited

U.S. PATENT DOCUMENTS

| | | | | |
|---|---|---|---|---|
| 5,922,591 A | * | 7/1999 | Anderson | ........... B01F 11/0071 |
| | | | | 422/504 |
| 6,087,182 A | * | 7/2000 | Jeng | ........................ G01N 21/05 |
| | | | | 356/72 |
| 6,637,463 B1 | | 10/2003 | Lei et al. | |

(Continued)

FOREIGN PATENT DOCUMENTS

| | | |
|---|---|---|
| EP | 0501796 A2 | 9/1992 |
| WO | WO-2002/10732 | 2/2002 |

(Continued)

*Primary Examiner* — Jennifer Wecker
(74) *Attorney, Agent, or Firm* — Fenwick & West LLP

(57) ABSTRACT

This disclosure relates to an apparatus for simultaneously filling a plurality of sample chambers. In one aspect, the apparatus comprises a common fluid source and a plurality of independent, continuous fluidic pathways. Each independent, continuous fluidic pathway comprises a sample chamber and a pneumatic compartment. The sample chamber is connected to the common fluid source, and the pneumatic compartment is connected to the sample chamber. The sample chamber comprises, in part, an assay chamber. The assay chamber comprises a monolithic substrate and a plug. In some embodiments, the assay chamber contains a magnetic mixing element. In some embodiments, the assay chamber is a double tapered chamber. In some embodiments, a ratio of a volume of the sample chamber to a volume of the pneumatic compartment is substantially equivalent for each fluidic pathway of the plurality of fluidic pathways.

27 Claims, 13 Drawing Sheets

(56) References Cited

U.S. PATENT DOCUMENTS

| | | |
|---|---|---|
| 6,843,281 B1 | 1/2005 | Barth et al. |
| 7,169,277 B2 | 1/2007 | Ausserer et al. |
| 7,179,423 B2 | 2/2007 | Böhm et al. |
| 7,763,453 B2 | 7/2010 | Clemmens et al. |
| 8,865,089 B2 | 10/2014 | Blatt et al. |
| 8,938,103 B2 | 1/2015 | Durand et al. |
| 9,089,883 B2 | 7/2015 | Stoeters et al. |
| 9,126,161 B2 | 9/2015 | Lee et al. |
| 9,186,638 B2 | 11/2015 | Claussen et al. |
| 9,200,315 B2 | 12/2015 | Jung et al. |
| 9,329,112 B2 | 5/2016 | Smith et al. |
| 9,339,602 B2 | 5/2016 | Carlisle et al. |
| 9,550,600 B2 | 1/2017 | Whitaker et al. |
| 9,771,553 B2 | 9/2017 | Vulto et al. |
| 2002/0124879 A1 | 9/2002 | Kaplan et al. |
| 2004/0184964 A1 | 9/2004 | Watanabe et al. |
| 2004/0208751 A1 | 10/2004 | Lazar et al. |
| 2005/0214947 A1 | 9/2005 | Cox |
| 2005/0244308 A1 | 11/2005 | Tanaami et al. |
| 2006/0090800 A1 | 5/2006 | Benerjee et al. |
| 2007/0280856 A1 | 12/2007 | Ulmanella et al. |
| 2007/0280857 A1 | 12/2007 | Song et al. |
| 2009/0047191 A1 | 2/2009 | Zainniev et al. |
| 2012/0082599 A1 | 4/2012 | Weber |
| 2013/0109106 A1* | 5/2013 | Klunder ............... B01L 3/0275 436/180 |
| 2016/0167047 A1 | 6/2016 | Weber et al. |
| 2016/0367981 A1* | 12/2016 | Wunderle ........... F16K 99/0015 |

FOREIGN PATENT DOCUMENTS

| | | |
|---|---|---|
| WO | WO 2002/012734 A1 | 2/2002 |
| WO | WO 2002/090771 A2 | 11/2002 |
| WO | WO-2002/094440 | 11/2002 |
| WO | WO-2007/064635 | 6/2007 |
| WO | WO-2007/143536 | 12/2007 |
| WO | WO-2007/143540 | 12/2007 |
| WO | WO-2008/127438 | 10/2008 |
| WO | WO 2009/112030 | 9/2009 |
| WO | WO-2014/190188 | 11/2014 |
| WO | WO 2018/001647 A1 | 1/2018 |
| WO | WO 2018/001648 A1 | 1/2018 |

* cited by examiner

REACTION WELL FOR ASSAY DEVICE

TECHNICAL FIELD

The present invention relates to the field of microfluidic devices that are capable of performing biological assays. In particular, the present disclosure is directed toward systems, devices, and methods for transmitting a fluid sample from a fluid source into multiple sample chambers configured to accommodate biological assays.

BACKGROUND

Many existing microfluidic devices are configured to transmit a fluid sample from one location within the microfluidic device, e.g., a common source, to one or more alternative locations within the microfluidic device, e.g., one or more sample chambers. In particular embodiments in which microfluidic devices are configured to transmit a fluid sample from one location within the microfluidic device to a single alternative location within the microfluidic device, existing microfluidic devices may use dead-end filling, in which the fluid sample is transferred into a closed system against an internal pressure of the closed system. Dead-end filling enables precise filling of the single location of the microfluidic device such that overflow of the fluid sample, and thus waste of fluid sample, is minimized. This precision provided by dead-end filling is particularly important in embodiments in which the fluid sample comprises expensive components.

In alternative embodiments in which microfluidic devices are configured to transmit a fluid sample from one location within the microfluidic device to multiple alternative locations within the microfluidic device, this transfer of the fluid sample is oftentimes performed asynchronously such that one or more of the locations completes filling at different times. Asynchronous completion of filling is problematic in embodiments in which the microfluidic device is used to perform assays, because the reliability of the assay results depends upon the uniformity of the variables that affect the results, such as reaction timing. Furthermore, asynchronous filling of the multiple locations of the microfluidic device may result in imprecise filling of one or more of the multiple locations of microfluidic device such that overflow of the fluid sample, and thus waste of fluid sample, occurs. Not only is this particularly undesirable in embodiments in which components of the fluid sample are expensive, but in embodiments in which the microfluidic device is used to perform assays, imprecise filling can increase the likelihood of heterogeneity of the fluid sample across the multiple locations, thereby further tarnishing the reliability of the assay results. In addition to these shortcomings of the existing microfluidic devices described above, many existing microfluidic devices also do not include built-in features to facilitate actuation of assays.

The novel devices described herein include microfluidic devices that are configured to control transmission of a fluid sample from a common fluid source to multiple sample chambers using dead-end filling, such that the multiple sample chambers are filled concurrently. The devices described herein enable precise filling of the multiple sample chambers such that overflow of the fluid sample, and thus waste of the fluid sample is minimized. Furthermore, concurrent filling of the multiple sample chambers, as enabled by the devices described herein, increases the likelihood of homogeneity of the fluid sample across the multiple sample chambers, and improves the uniformity of reaction timnng across the multiple sample chambers, thereby improving the reliability of assay results generated by the microfluidic device.

In certain embodiments, the novel devices described herein also include features to facilitate actuation of assays. For instance, in certain embodiments, one or more of the sample chambers of the novel devices described herein comprise a double tapered chamber that minimizes the trapping of bubbles within the sample chamber during filling with the fluid sample. Minimizing bubble trapping is advantageous during assay actuation because in some embodiments, bubbles interfere with the results of the assay.

SUMMARY

The present disclosure relates generally to microfluidic devices that transmit a fluid sample from a fluid source into multiple sample chambers configured to accommodate biological assays.

In one aspect, the disclosure provides an apparatus that comprises a common fluid source and a plurality of independent, continuous fluidic pathways connected to the common fluid source. Each independent, continuous fluidic pathway comprises a sample chamber and a pneumnatic compartment. The sample chamber, having a fluid volume, is connected to the common fluid source. The pneumatic compartment, having a pneumatic volume, is connected to the sample chamber, and thereby is indirectly connected to the common fluid source. Each fluidic pathway of the plurality of independent, continuous fluidic pathways is a closed system excluding the connection between the sample chamber and the common fluid source. In some embodiments, the fluid volume of one fluidic pathway of the apparatus is greater than the fluid volume of another fluidic pathway of the apparatus. To support concurrent delivery of a sample to each sample chamber, the ratio of fluid volume to pneumatic volume is substantially equivalent for each fluidic pathway of the plurality of fluidic pathways.

In some embodiments of the apparatus, the sample chamber comprises an assay chamber and an entry conduit that connects the common fluid source to the assay chamber. In certain implementations, the assay chamber volume is between 1 µL and 35 µL. Similarly, the pneumatic compartment may comprise an air chamber and a pneumatic conduit that connects the sample chamber to the air chamber. Therefore, each fluidic pathway may comprise an entry conduit, an assay chamber, a pneumatic conduit, and air chamber.

In some embodiments, the assay chamber comprises a double tapered chamber that in turn comprises a tapered inlet, a tapered outlet, and two curved boundaries. The tapered inlet is in fluidic communication with a terminus of the entry conduit of the fluidic pathway. Similarly, the tapered outlet is in fluidic communication with a terminus of the pneumatic compartment, frequently with a terminus of the pneumatic conduit. The two curved boundaries extend from the tapered inlet to the tapered outlet such that together, the two curved boundaries enclose the volume of the assay chamber. Additionally, the tapered inlet and the tapered outlet are separated by the largest dimension of the assay chamber volume. Furthermore, each curved boundary comprises a midpoint, and a distance between the two curved boundaries decreases as the boundaries curve from the midpoint toward the tapered inlet and from the midpoint toward the tapered outlet.

In certain embodiments, the assay chamber comprises a first bounding surface formed in a monolithic substrate, and a second bounding surface formed by a plug. The plug comprises a body and a cap. The body of the plug protrudes into the monolithic substrate of the assay chamber at a depth such that the assay chamber volume can be readily changed by altering the depth at which the body of the plug protrudes into the monolithic substrate of the assay chamber. In particular, the cap of the plug forms the second bounding surface of the assay chamber. In further embodiments, a film may form a third bounding surface of the assay chamber such that the first bounding surface, the second bounding surface, and the third bounding surface together enclose the assay chamber volume. In some embodiments, the plug cap comprises an internal cavity configured to hold one or more dried reagents for use in an assay to take place in the assay chamber. Additionally, a magnetic mixing element may be located in the assay chamber to facilitate actuation of an assay in the assay chamber.

In certain aspects of the disclosed apparatus, one or more films may be adhered to a portion of the apparatus. For example, a first film may be adhered to a surface of at least a portion of the apparatus such that the first film forms one wall of one or more chambers, compartments, or conduits of the apparatus. In certain embodiments discussed in further detail below, it may be desirable to seal a portion of one or more of the fluidic pathways of the apparatus using heat. Accordingly, in such embodiments, a second film, having a higher melting temperature, may be adhered to the first film.

In another, distinct aspect, the disclosure provides a method of simultaneously filling a plurality of sample chambers. The method includes providing an apparatus according to one or more of the embodiments described above. For use in simultaneous filling of the plurality of the sample chambers, the common fluid source of the provided apparatus contains a fluid sample, and each independent, continuous fluidic pathway of the provided apparatus contains a gas, such as, for example, air. After provision of the apparatus, a supply pressure is applied to the fluid sample in the common fluid source, thereby forcing the fluid sample from the common fluid source, into the sample chamber of each fluidic pathway of the apparatus. In certain embodiments, the supply pressure is applied at a constant pressure. In alternative embodiments, the supply pressure is applied from a lower pressure to a higher pressure. In certain aspects, the fluid sample travels to the plurality of sample chambers via the entry conduits against a gravitational force. This transmission of the fluid sample into the sample chamber of each fluidic pathway of the apparatus compresses the gas within the fluidic pathways toward the pneumatic compartments of the fluidic pathways. This m turn causes an increase in the internal pressure in the pneumatic compartments of the fluidic pathways. When the internal pressure in a pneumatic compartment equals the supply pressure, the fluid sample stops flowing from the common fluid source into the fluidic pathway.

In some embodiments of the disclosed method, at least two sample chambers of the provided apparatus differ in volume. For example, a fluid volume of a sample chamber of a first fluidic pathway of the provided apparatus may be greater than a fluid volume of a sample chamber of a second fluidic pathway of the provided apparatus. Generally, a rate of flow from the common fluid source into each sample chamber of the plurality of sample chambers is proportional to a fluid volume of the sample chamber. Additionally, as noted above, the ratio of fluid volume to pneumatic volume is substantially equivalent for each fluidic pathway of the provided apparatus. Therefore, sample chambers of the provided apparatus, including the differentially sized sample chambers of the first fluidic pathway and the second fluidic pathway, fill at a substantially proportional rate such that the sample chambers fill simultaneously.

As described above, certain embodiments of the apparatus provided by the disclosed method may comprise one or more sample chambers that in turn comprise a double tapered chamber. In such embodiments in which one or more sample chambers of the provided apparatus comprise a double tapered chamber, the two curved boundaries of the double tapered chamber slow the rate of fluid advance at the leading front meniscus of the fluid sample, such that when the fluid sample reaches the tapered outlet, the meniscus of the fluid sample is substantially symmetric with respect to the largest dimension of the assay chamber, thereby minimizing the trapping of bubbles within the assay chamber during filling.

Also as described above, in certain aspects, it may be desirable to seal the fluidic pathways of the apparatus using heat. In such aspects, the method disclosed herein further comprises sealing each fluidic pathway of the plurality of fluidic pathways when the fluid sample stops flowing from the common fluid source into the fluidic pathway. This step of sealing can be performed by heat staking.

In yet another aspect, the disclosure provides an apparatus for rehydrating a dried reagent that is distinct from the various embodiments of the apparatus described above. In such aspects, the apparatus at issue comprises an assay chamber. The assay chamber comprises a first bounding surface formed in a monolithic substrate and a second bounding surface formed by a plug. The plug comprises a body and a cap. The body of the plug protrudes into the monolithic substrate of the assay chamber at a depth such that the assay chamber volume can be readily changed by altering the depth at which the body of the plug protrudes into the monolithic substrate of the assay chamber. In particular, the cap of the plug forms the second bounding surface of the assay chamber. Together, the first bounding surface and the second bounding surface of the assay chamber enclose a volume of the assay chamber. An internal cavity of the formed in the cap of the plug can hold one or more dried reagents for use in an assay to occur in the assay chamber. The assay chamber contains a magnetic mixing element within the volume of the assay chamber. The magnetic mixing element is capable of gyration within the assay chamber volume.

In certain embodiments of the apparatus fir rehydrating a dried reagent, the assay chamber comprises a third bounding surface of a film. In such embodiments, the first bounding surface, the second bounding surface, and the third bounding surface together enclose the assay chamber volume.

In yet another distinct aspect, the disclosure provides a method of solubilizing a dried reagent. This method includes providing the apparatus for rehydrating a dried reagent according to one of the embodiments described above. The method further comprises filling the assay chamber with a fluid and inducing gyration of the magnetic mixing element within the assay chamber of the apparatus by rotating a magnet exterior to the assay chamber. This gyration of the magnetic mixing element within the assay chamber solubilizes the reagent within the fluid.

BRIEF DESCRIPTION OF THE DRAWINGS

The present application is further understood when read in conjunction with the appended drawings. For the purpose of illustrating the subject matter, there are shown in the drawings exemplary embodiments of the subject matter, however, the presently disclosed subject matter is not limited to the specific methods, devices, and systems disclosed. In addition, the drawings are not necessarily drawn to scale. In the drawings.

DETAILED DESCRIPTION

Figure 1:
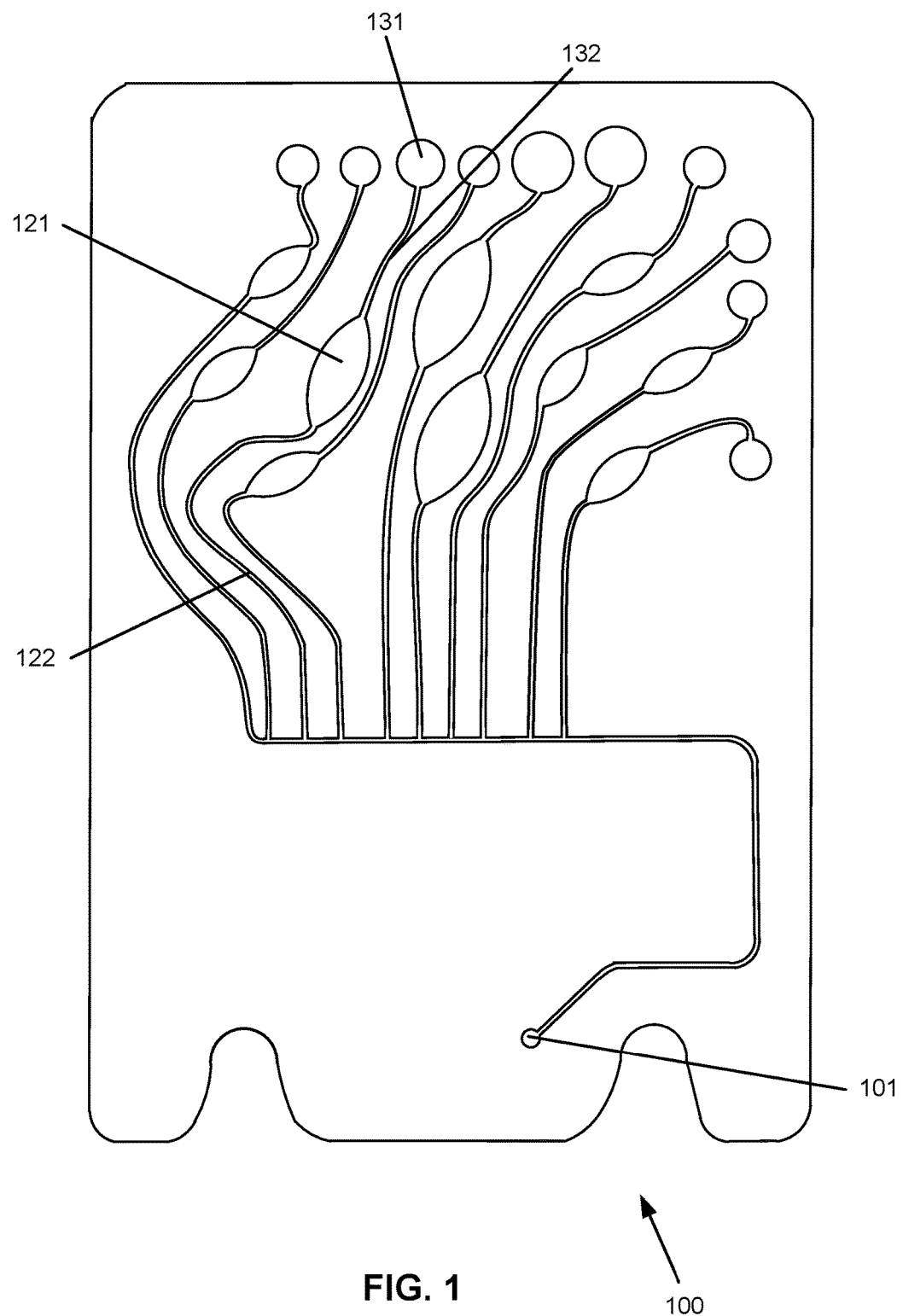
FIG. 1 is an illustration of an apparatus for transmitting a fluid sample from a fluid source into multiple sample chambers, in accordance with an embodiment.

Systems, devices, and methods for transmitting a fluid sample from a fluid source into multiple sample chambers, are provided herein. In some embodiments, the devices include a plurality of independent, continuous fluidic pathways, each fluidic pathway comprising a sample chamber connected to a fluid source, and a pneumatic compartment connected to the sample chamber. The ratio of the volume of the sample chamber to the volume of the pneumatic compartment is substantially equivalent for each fluidic pathway sharing the common fluidic source. In some embodiments, the sample chamber of each fluidic pathway includes a double tapered chamber, a magnetic mixing element, and/or a plug. In some embodiments, the methods include simultaneously filling the plurality of sample chambers with the fluid sample. In some embodiments, the methods include filling the sample chambers with a fluid sample, and mixing the fluid sample in the sample chambers using a magnetic mixing element held within each sample chamber.

Before the disclosed embodiments are described in greater detail, it is to be understood that this disclosure is not limited to particular embodiments described, and as such can, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present disclosure. The upper and lower limits of these smaller ranges can independently be included in the smaller ranges and are also encompassed within the present disclosure, subject to any specifically excluded limit in the stated range. Where the stated range includes one or both of the limits, ranges excluding either or both of those included limits are also included in the present disclosure.

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc), but some experimental error and deviation should, of course, be allowed for.

Unless defined otherwise, all technical and scientific terms used herein have the same meaning as commonly understood by one of ordinary skill in the art to which these disclosed embodiments belong. Although any methods and materials similar or equivalent to those described herein can also be used in the practice or testing of the disclosed embodiments, representative illustrative methods and materials are now described. Any recited method can be carried out in the order of events recited or in any other order which is logically possible.

It is noted that, as used herein and in the appended claims, the singular forms "a," "an," and "the" include plural referents unless the context clearly dictates otherwise.

Systems

Included in the disclosure are systems, devices, and methods for transmitting a fluid sample from a fluid source into multiple sample chambers. Systems according to the subject embodiments include a fluid source and a plurality of independent, continuous fluidic pathways, each fluidic pathway comprising a sample chamber connected to the fluid source, and a pneumatic compartment connected to the sample chamber. The fluid source, the sample chamber, and the pneumatic compartment are used in conjunction with one another to transmit a fluid sample from the fluid source into the sample chamber.

FIG. 1 is an illustration of an apparatus 100 for transmitting a fluid sample from a fluid source into multiple sample chambers, in accordance with an embodiment. The apparatus includes a common fluid source 101 connected to a plurality of independent, continuous fluidic pathways. In alternative embodiments, rather than including the ten fluidic pathways shown in FIG. 1, the apparatus may include any number of fluidic pathways. For example, in some embodiments, the apparatus may include two, five, twelve, or twenty independent, continuous fluidic pathways.

Each independent, continuous fluidic pathway 110 of the plurality of independent, continuous fluidic pathways comprises a sample chamber and a pneumatic compartment. In some embodiments, each sample chamber comprises an entry conduit 122 and an assay chamber 121. In some further embodiments, each pneumatic compartment comprises a pneumatic conduit 132 and an air chamber 131. Therefore, in such implementations, each fluidic pathway comprises an entry conduit, an assay chamber, a pneumatic conduit, and an air chamber.

The common fluid source is an inlet, chamber, conduit, or the like capable of supplying a fluid sample to each fluidic pathway of the apparatus at a supply pressure. The common fluid source is connected to, and is in fluidic communication with, each fluidic pathway of the plurality of fluidic pathways. In other implementations, as illustrated in FIG. 1, the common fluid source is connected to, and is in fluidic communication with, the entry conduit of each fluidic pathway. Accordingly, the common fluid source can supply a fluid sample to each fluidic pathway of the apparatus via its respective entry conduit.

The entry conduit of each fluidic pathway is in turn connected to, and in fluidic communication with, the assay chamber of the fluidic pathway. The assay chamber of the fluidic pathway is in turn connected to, and in fluidic communication with, the pneumatic conduit of the fluidic pathway. In certain implementations, such as illustrated in FIG. 1, the pneumatic compartment comprises a pneumatic conduit that is in turn connected to, and in fluidic communication with, the air chamber of the fluidic pathway. In other implementations the pneumatic compartment can be comprised of a single structure directly connected to the sample chamber, or the assay chamber thereof.

The terms "fluidic connection," and "fluidic continuity" as used herein, refers to any duct, channel, tube, pipe, or pathway through which a substance, such as a liquid, gas, or solid may pass substantially unrestricted when the pathway is open. When the pathway is closed, the substance is substantially restricted from passing through. Typically, limited diffusion of a substance through the material of a substrate, which may or may not occur depending on the compositions of the substance and materials, does not constitute fluidic communication.

Due to the continuity of each fluidic pathway, a fluid sample from the common fluid source can travel throughout the fluidic pathway. Specifically, a fluid sample from the common fluid source can travel through the entry conduit, into the assay chamber, through the pneumatic conduit, and into the air chamber of each fluidic pathway. However, in some embodiments it may be desirable to confine the fluid sample to the assay chambers of the apparatus such that the fluid sample is not lost to the pneumatic compartment. Such embodiments are described in greater detail below. In some embodiments, the apparatus is oriented such that the fluid sample travels into the assay chamber via the entry conduit against a gravitational force.

Excluding the connection between the common fluid source and the entry conduit of each fluidic pathway, each fluidic pathway is a closed system. As used herein, the term "closed system" refers to a system that can exchange heat and energy but not matter, with its surroundings. The term closed system is not intended to exclude limited permeability of gases, such as water vapor or oxygen into the substrate in which the fluidic pathway is formed. In other words, matter contained within a fluidic pathway cannot travel into or out of the fluidic pathway, except via the connection between the common fluid source and the entry conduit of the fluidic pathway. In certain methods of using the apparatus described herein, the fluidic connection between the common fluid source and each of the fluidic pathways is sealed, e.g. by heat staking, during operation of the method.

By sealing off a connection between the common fluid source and an entry conduit of a fluidic pathway, the fluidic pathway becomes a completely closed system from which matter cannot travel in or out, and for which, devoid of any changing variables, internal pressure within the fluidic pathway remains constant. One such embodiment of sealing off a connection between the common fluid source and an entry conduit of a fluidic pathway is discussed in greater detail below with regard to FIGS. 2E and 2F.

As noted above, each fluidic pathway includes a sample chamber and a pneumatic compartment. In turn, each sample chamber includes an entry conduit and an assay chamber, and each pneumatic compartment includes a pneumatic conduit and an air chamber.

The entry conduit is configured to transport a fluid sample from the common fluid source into the assay chamber of the fluidic pathway. The assay chamber is configured to contain an assay. In some embodiments, an assay chamber may include features to facilitate the assay. For example, in some embodiments discussed in further detail below with regard to FIG. 3B, each assay chamber is configured to minimize formation of bubbles during transmission of the fluid sample into the assay chamber. This feature is advantageous during assay actuation because in some embodiments, bubbles prevent complete filling of the chamber or otherwise interfere with the results of the assay. Additionally, in some embodiments discussed in further detail below with regard to FIGS. 4-7, each assay chamber is configured to include a plug, and/or to contain dried reagents and/or a magnetic mixing element to facilitate assay actuation.

The sample chamber is fluidically connected to the pneumatic compartment. In those embodiments comprising an entry conduit and an assay chamber, the assay chamber is connected to a pneumatic compartment of the fluidic pathway. As mentioned above, the pneumatic compartment can include a pneumatic conduit and an air chamber. The pneumatic conduit connects the assay chamber to the air chamber of the fluidic pathway.

In embodiments in which each assay chamber of an apparatus is configured to contain an assay as described above, it may be beneficial to control a rate of flow of a fluid sample into the assay chambers to ensure that each assay chamber is filled with a precise amount of fluid sample, and to ensure that the composition of the fluid sample is homogenous across all assay chambers of the apparatus. This enables standardization of assays that may take place in the assay chambers, in some embodiments. Accordingly, the pneumatic compartment of each fluidic pathway is configured to control the flow rate of a fluid sample into the assay chamber of the fluidic pathway according to the internal pressure of the pneumatic compartment. The configuration and the function of the pneumatic compartments are discussed in greater detail below.

Both the sample chamber and the pneumatic compartment of each fluidic pathway have a volume. The sample chamber has a volume hereinafter referred to as the "fluid volume." The fluid volume of a fluidic pathway includes the volume of the entry conduit and the volume of the assay chamber of the fluidic pathway. Similarly, the pneumatic compartment has a volume hereinafter referred to as the "pneumatic volume." The pneumatic volume of a fluidic pathway includes the volume of the pneumatic conduit and the volume of the air chamber of the fluidic pathway. In order to achieve concurrent filling of each sample chamber, particularly when the volume of the sample chambers vary across the plurality of fluid pathways, the ratio of the fluid volume to the pneumatic volume is the same for each fluidic pathway sharing a common fluid source.

Prior to the introduction of a fluid sample into each fluidic pathway of an apparatus by a common fluid source, the fluidic pathways contain a gas, such as, e.g., air, at an initial air pressure. Throughout this disclosure air should be interpreted to encompass a mixture of atmospheric gasses or any other gas mixture or pure gas that is compatible with the assays carried out in the apparatus. Furthermore, as one skilled in the art would understand, any gas can be used in place of air in the fluidic pathways of the devices and methods described herein. For example, in some embodiments, air can be substituted with another gas. e.g., an inert gas such as, e.g, nitrogen or argon.

The initial pressure of air within a fluidic pathway in part determines the internal pressure of the fluidic pathway. When a fluid sample is introduced into the fluidic pathways by the common fluid source, the air within each fluidic pathway is displaced within the fluidic pathway by the advancing fluid sample. Specifically, the advancing fluid sample enters each fluidic pathway via an entry conduit of the fluidic pathway and displaces the air within the fluidic pathway in a direction of the air chamber. As a result of this displacement, the volume that is occupied by the air in the fluidic pathway decreases. As a result of this decreased volume occupied by the air, the pressure of the air, and thus the internal pressure of the fluidic pathway, increases. Specifically, the internal pressure increases proportionally to the decrease in the volume occupied by the air.

The balance of supply pressure and internal pressure within a fluidic pathway determines a rate of flow of a fluid sample within the fluidic pathway Specifically, if the internal pressure within the fluidic pathway is less than a pressure at which the fluid sample is supplied to the fluidic pathway, the fluid sample continues to advance within the fluidic pathway, and continues to displace the air contained within the fluidic pathway such that the internal pressure increases. However, the closer in value that the internal pressure is to the supply pressure of the fluid sample, the more pressure the air exerts on the fluid sample within the fluidic pathway, and the more the internal pressure retards a rate of flow of the fluid sample within the fluidic pathway. Once the internal pressure within the fluidic pathway equals the supply pressure of the fluid sample, the fluid sample stops flowing into the fluidic pathway. Accordingly, by controlling a volume in which air is contained within a fluidic pathway, and thereby controlling the internal pressure of the fluidic pathway, it is possible to control the rate of flow of the fluid sample within the fluidic pathway.

It may be desirable to control the rate of flow of a fluid sample within a fluidic pathway in a variety of circumstances Particularly, in certain embodiments, it may be desirable to control a rate of flow of a fluid sample within a fluidic pathway such that the fluid sample is confined to the sample chamber of the fluidic pathway and does not flow into the pneumatic compartment of the fluidic pathway. In other words, it may be desirable to control the rate of flow of a fluid sample within a fluidic pathway such that the sample chamber (and in some embodiments, the assay chamber in particular) is substantially filled with the fluid sample. As used herein, the term "substantially filled" or "substantially full" means that at least 90% of the fluid volume of the sample chamber contains the fluid sample, and at most 10% of the pneumatic volume of the pneumatic compartment contains the fluid sample. In particular, filling 10% or less of the pneumatic volume of the pneumatic compartment with the fluid sample does not disrupt the operation of the apparatus.

To substantially fill a sample chamber of a fluidic pathway, the pressure at which the fluid sample is supplied to the sample chamber must equal the internal pressure within the fluidic pathway when the sample chamber is substantially filled with the fluid sample. Furthermore, because the fluid sample is confined to the sample chamber of the fluidic pathway when the sample chamber is substantially filled, the air contained within the fluidic pathway is compressed into the pneumatic compartment of the fluidic pathway. Thus, to substantially fill a sample chamber of a fluidic pathway, the pressure at which the fluid sample is supplied to the sample chamber must equal the internal pressure contained within the pneumatic compartment of the fluidic pathway when the sample chamber is substantially filled with the fluid sample.

As mentioned above, internal pressure depends, in part, on the volume of air being displaced from the sample chamber and, in part, on the volume confining the displaced air. Thus when a fluid sample substantially fills the sample chamber of a fluidic pathway, the displaced air is confined within the pneumatic compartment, and the internal pressure depends on the pneumatic volume of the pneumatic compartment and on the fluid volume of the sample chamber.

Therefore, to achieve a balance between the internal pressure and the supply pressure of the fluid sample when the sample chamber is substantially filled with the fluid sample, the pneumatic volume of the fluidic pathway can be intentionally selected in view of the fluid volume of the sample chamber and the supply pressure. Additionally, as an initial internal pressure within the fluidic pathway and the supply pressure of the fluid sample are also factors in achieving equivalence between the internal pressure contained within the pneumatic volume and the supply pressure of the fluid sample, the ambient internal pressure within the fluidic pathway and the supply pressure of the fluid sample can also be intentionally selected to ensure that the supply pressure of the fluid sample equals the internal pressure contained within the pneumatic compartment when the sample chamber is substantially filled with the fluid sample. This equivalence between the internal pressure and the supply pressure results in a net zero force on the fluid sample contained within the fluidic pathway, thereby stopping the flow of the fluid sample into the fluidic pathway just when the sample chamber is substantially filled.

In further embodiments, it may be desirable to control the rate of flow of a fluid sample within the multiple fluidic pathways of the apparatus such that the sample chamber of each fluidic pathway fills simultaneously. However, as noted above, in some embodiments, the fluid volume of each fluidic pathway of the apparatus can differ. This variation in fluid volumes means that if a fluid sample flows into each fluidic pathway at the same rate, the sample chambers will not fill simultaneously. Rather, if the fluid sample flows into fluidic pathways of varying fluid volumes at the same rate, the fluidic pathways with smaller fluid volumes will fill with the fluid sample before the fluidic pathways with larger fluid volumes.

To ensure that the sample chamber of each fluidic pathway fills simultaneously regardless of its fluid volume, the fluidic pathways can be configured such that a rate of flow of a fluid sample into each fluidic pathway is proportional to the fluid volume of the fluidic pathway. For example, a first fluidic pathway with a fluid volume that is twice the fluid volume of a second fluidic pathway will be configured such that a rate of flow of a fluid sample into the first fluidic pathway is twice the rate of flow of the fluid sample into the second fluidic pathway. In this way, a sample chamber of the first fluidic pathway and a sample chamber of the second fluidic pathway will fill simultaneously.

As described above, a rate at which a fluid sample from the common fluid source flows into a fluidic pathway depends on an internal pressure of the fluidic pathway and the supply pressure. Specifically, the closer in value that the internal pressure is to the supply pressure, the more the internal pressure retards a rate of flow of the fluid sample within the fluidic pathway. Furthermore, as described above, the internal pressure of the contained air depends, in part, on a volume in which the air is contained. Specifically, air that is displaced into a portion of a fluidic pathway with a smaller volume will have a greater increase in pressure than a similar volume of air that initially is displaced into a portion of the fluidic pathway with a larger volume.

Therefore, to configure the fluidic pathways such that a rate of flow of a fluid sample into each fluidic pathway is proportional to the fluid volume of the fluidic pathway, each fluidic pathway can be configured such that the volume in which the air is contained is proportional to the fluid volume of the fluidic pathway. In embodiments in which the sample chamber of the fluidic pathway is the portion of the fluidic pathway being filled with the fluid sample, the volume in which the air is contained is the pneumatic volume of the fluidic pathway. Thus in such embodiments, to achieve an inverse proportionality between the internal pressure of a fluidic pathway and the fluid volume of the fluidic pathway, each fluidic pathway is configured such that the pneumatic volume of the fluidic pathway is proportional to the fluid volume of the fluidic pathway.

Furthermore, to achieve simultaneous filling of the sample chamber of each fluidic pathway of an apparatus, this proportionality between the fluid volume of the fluidic pathway and the pneumatic volume of the fluidic pathway must be the same for all of the fluidic pathways of the apparatus. Specifically, a ratio of the fluid volume to the pneumatic volume of a fluidic pathway must be substantially equivalent for each fluidic pathway of the apparatus. Note that as used herein, "substantially equivalent" means that the ratios of the fluid volume to the pneumatic volume differ by no more than +/−10%.

In certain embodiments, the volumes of the entry conduit and the pneumatic conduit are negligible relative to the volumes of the assay chamber and the air chamber, respectively. Specifically, as used herein, "negligible" means that the volume of an entry conduit of a fluidic pathway comprises no more than 10% of the volume of an assay chamber of the fluidic pathway, and similarly, the volume of the pneumatic conduit of a fluidic pathway comprises no more than 10% of the volume of an air chamber of the fluidic pathway. Therefore, in such embodiments, the fluid volume of the sample chamber is comprised, in large part, of the volume of the assay chamber, and in small part, of the volume of the entry conduit. Similarly, in such embodiments, the pneumatic volume of the pneumatic compartment is comprised, in large part, of the volume of the air chamber, and in small part, of the volume of the pneumatic conduit.

In some embodiments, the fluid volume of one or more fluidic pathways of an apparatus can differ. For example, a fluid volume of a first fluidic pathway of the apparatus can be greater than a fluid volume of a second fluidic pathway of the apparatus. This difference in fluid volumes across the fluidic pathways of the apparatus can be the result of a difference in volumes of the assay chambers and/or a difference in volumes of the entry conduits of the fluidic pathways.

In embodiments in which the fluid volume of one or more fluidic pathways of an apparatus differs, the pneumatic volume of the one or more fluidic pathways of the apparatus would also differ for reasons discussed in further detail below. A difference in pneumatic volumes across the fluidic pathways of the apparatus can be the result of a difference in volumes of the air chambers and/or a difference in volumes of the pneumatic conduits of the fluidic pathways.

In embodiments in which the volumes of the entry conduits and the pneumatic conduits of the fluidic pathways are negligible relative to the volumes of the assay chambers and the air chambers, to enable simultaneous filling of the sample chamber of each fluidic pathway, a ratio of the volume of the assay chamber to the air chamber of a fluidic pathway may be substantially equivalent for each fluidic pathway.

Methods

FIGS. 2A-2F depict the apparatus of FIG. 1 at a plurality of sequential time points during simultaneous filling of the sample chambers with a fluid sample from the common fluid source, in accordance with an embodiment. In some embodiments, the apparatus is oriented during filling of the sample chambers such that the fluid sample travels into the sample chambers against a gravitational force. As described above with regard to FIG. 1, the fluid volume of each fluidic pathway of the apparatus may vary. Therefore, to enable simultaneous filling of the sample chamber of each fluidic pathway of the apparatus, a ratio of the fluid volume to the pneumatic volume is substantially equivalent for each fluidic pathway of the apparatus.

As shown in the legend at the bottom left-hand corner of FIGS. 2A-2F, air is denoted within the fluidic pathways by white space. Contrastingly, the fluid sample is denoted within the common fluid source and the fluidic pathways by black space.

Figure 2A:
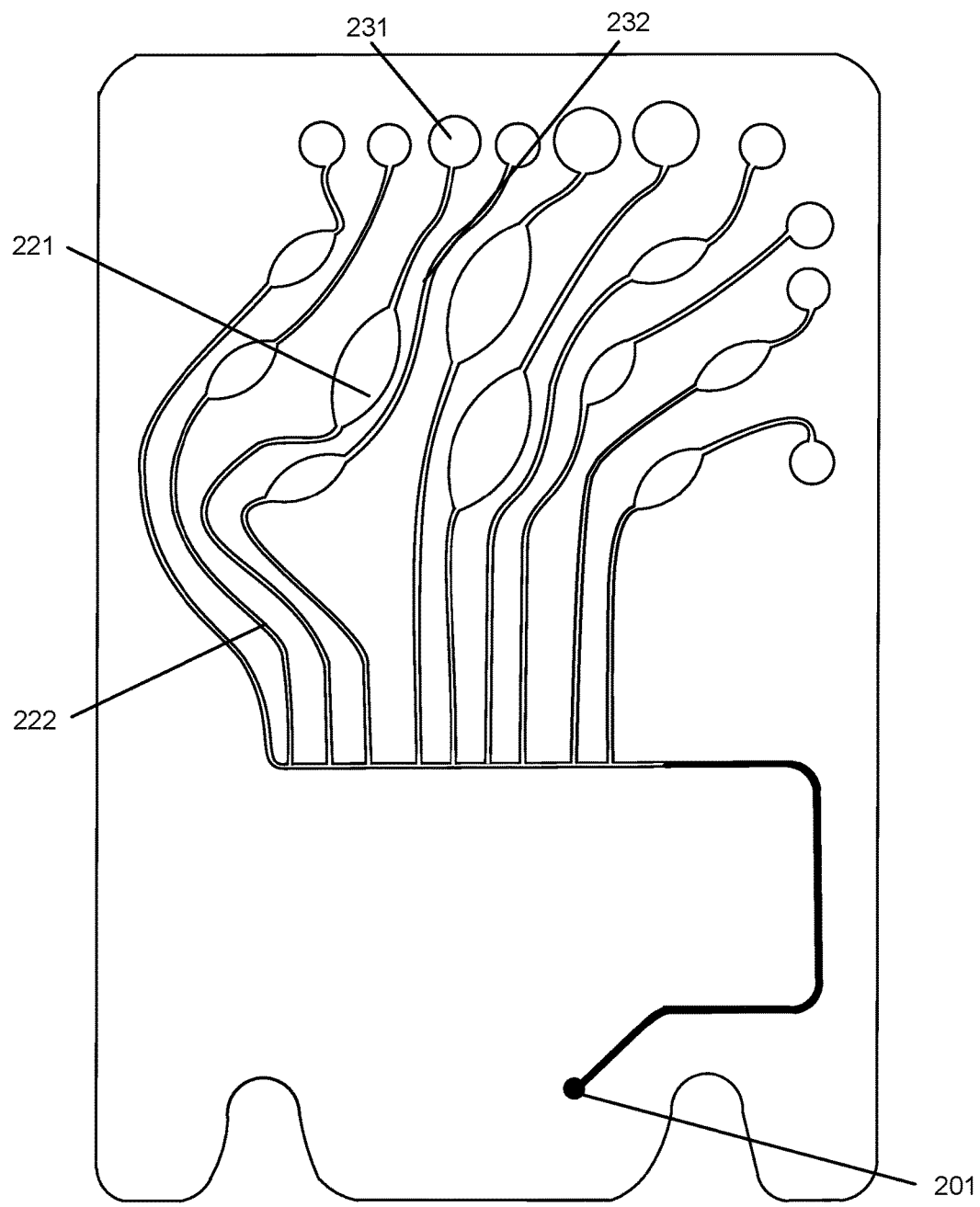
FIG. 2A depicts an apparatus at a time A during simultaneous filling of sample chambers of the apparatus with a fluid sample, in accordance with an embodiment.

FIG. 2A depicts the apparatus 200 at a time A. At the time A, the fluidic pathways are filled with air 250. The air contained within the fluidic pathways at the time A is has an initial air pressure that contributes, at least in part, to the internal pressure of the fluidic pathways. At the time A, the common fluid source 201 supplies the fluid sample 260 to the fluidic pathways at a supply pressure that is greater than the internal pressure within the fluidic pathways. Because the supply pressure of the fluid sample is greater than the internal pressure within the fluidic pathways, the fluid sample advances from the common fluid source toward the entry conduit 222 of each fluidic pathway. As the fluid sample advances within the apparatus, the air contained within the fluidic pathways is displaced by the fluid sample toward the air chambers of the apparatus. This displacement of the air into a smaller volume causes the pressure of the air, and thus the internal pressure, to increase. As the internal pressure increases, the air exerts an increasing amount of pressure on the advancing fluid sample, thereby slowing the rate of flow of the fluid sample.

Figure 2B:
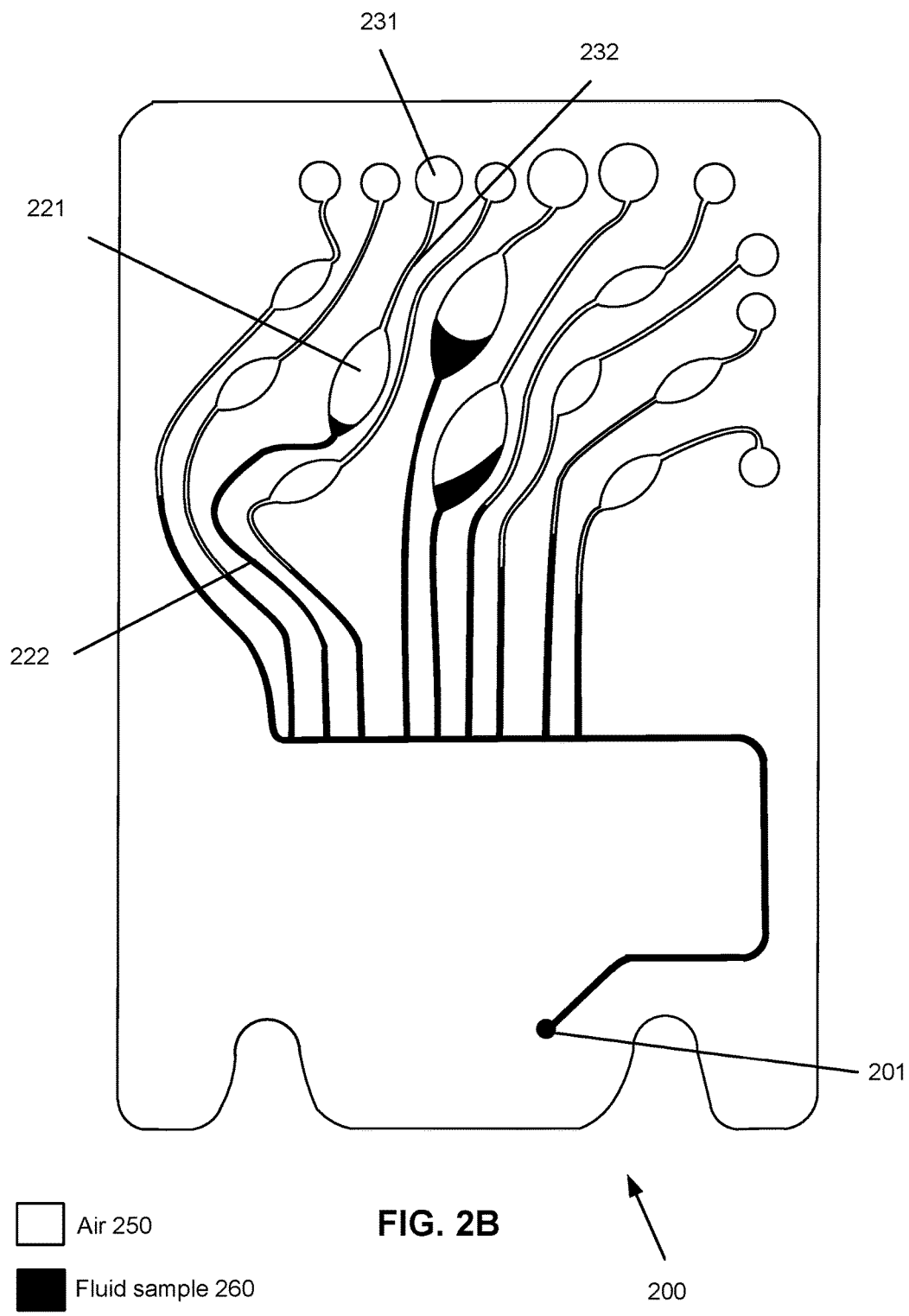
FIG. 2B depicts an apparatus at a time B during simultaneous filling of sample chambers of the apparatus with a fluid sample, in accordance with an embodiment.

FIG. 2B depicts the apparatus 200 at a time B that is subsequent to the time A. At the time B, the common fluid source 201 continues to supply the fluid sample 260 to the fluidic pathways at a supply pressure.

In some embodiments, throughout the filling of the sample chamber of each fluidic pathway, the supply pressure of the fluid sample is applied at a constant pressure. In other words, the supply pressure at one time point is equivalent to the supply pressure at all other time points.

In alternative embodiments, the supply pressure is applied in a ramping fashion, such that the supply pressure increases over time from a lower pressure to a higher pressure. In other words, the supply pressure at a first time point is greater than the supply pressure at a second time point subsequent to the first time point. In such embodiments in which the supply pressure is applied in a ramping fashion, the supply pressure may increase linearly over time from a lower pressure to a higher pressure. In alternative embodiments, the ramping of the supply pressure may follow a parabolic trajectory. In alternative embodiments, the ramping of the supply pressure may follow any alternative trajectory. In embodiments in which the supply pressure is applied in a ramping fashion, this ramping of the supply pressure can dislodge air bubbles that may have formed within a sample chamber during filling, because the increasing supply pressure compresses and detaches the bubbles from their positions within the sample chamber, enabling the bubbles to be released into the pneumatic compartment. In particular embodiments in which the fluid sample travels into the sample chambers against a gravitational force, this orientation of the apparatus aids the detached bubbles in traveling to the top of the sample chamber and into the pneumatic compartment.

Turning back to FIG. 2B, at the time B, the supply pressure is still greater than the internal pressure within the fluidic pathways. Because the supply pressure of the fluid sample is still greater than the internal pressure within the fluidic pathways, the fluid sample continues to advance into each fluidic pathway toward the air chamber 231 of the fluidic pathway Specifically, as shown in FIG. 2B, the fluid sample has advanced into at least the entry conduit 222 of each fluidic pathway. Furthermore, the fluid sample has advanced into the assay chambers 221 of a portion of the fluid pathways. Accordingly, air is trapped within the fluidic pathways. As the volume of fluid sample supplied to the fluidic pathways via the common fluid source increases, and accordingly as the fluid sample advances within the fluidic pathways towards the air chambers, the air contained within each fluidic pathway is displaced into a smaller volume within the fluidic pathway. Accordingly, the internal pressure of the fluidic pathway increases. As a result of this increase in internal pressure of each fluidic pathway, the air exerts an increasing amount of pressure on the advancing fluid sample in the fluidic pathway, thereby decreasing the rate of flow of the fluid sample in the fluidic pathway.

However, the internal pressure within each fluidic pathway does not increase uniformly across all of the fluidic pathways of the apparatus. Rather, an internal pressure of a fluidic pathway depends on the volume into which the air is displaced. Specifically, as the fluid travels through each of the channels, the air upstream of the fluid is compressed. The compressed gas generates a back-pressure that resists the advancing fluid flow. This back-pressure is inversely proportional to the ratio of the contained volume over the original volume in accordance with the ideal gas law. For example, fluid in a channel that is connected to a large pneumatic volume would experience a higher back-pressure than a fluid through a channel of the same length that is connected to a smaller pneumatic volume.

In turn, the velocity of the fluid is proportional to the difference between the pressure applied to the channel, and the back-pressure that comes from the compressed gas in the pneumatic volume and upstream channel. As such, fluid in a channel with a larger pneumatic volume would travel faster than fluid in a channel of the same size with a smaller pneumatic volume.

Furthermore, as the upstream gas volume is further compressed, the back-pressure increases proportionally. Since the velocity of the fluid is proportional to the pressure difference, the velocity of the fluid gradually decreases as the channels fill. The fluid flow stops when the pressure applied to the fluid is equal to the back-pressure from the compressed pneumatic volumes.

As described above with regard to FIG. 1, to enable simultaneous filling of the sample chamber of each fluidic pathway, in some embodiments of the apparatus, each fluidic pathway is configured such that the pneumatic volume of the fluidic pathway is proportional to the fluid volume of the fluidic pathway. For example, a fluidic pathway with a relatively large fluidic volume also has a relatively large pneumatic volume. Therefore, in such embodiments, because a rate of flow of a fluid sample in a fluidic pathway is proportional to the pneumatic volume of the fluidic pathway, the rate of flow of a fluid sample in a fluidic pathway is also proportional to the fluid volume of the fluidic pathway. In other words, fluidic pathways with a larger fluid volume experience a relatively greater rate of flow of a fluid sample than fluidic pathways with a smaller fluid volume. This phenomenon can be seen in FIG. 2B. Specifically, as seen in FIG. 2B, at the time B, the fluidic pathways with larger fluid volumes contain a larger volume of the fluid sample than the fluidic pathways with smaller fluid volumes because the fluidic pathways with larger fluid volumes experience a relatively greater rate of flow of the fluid sample than the fluidic pathways with smaller fluid volumes.

Figure 2C:
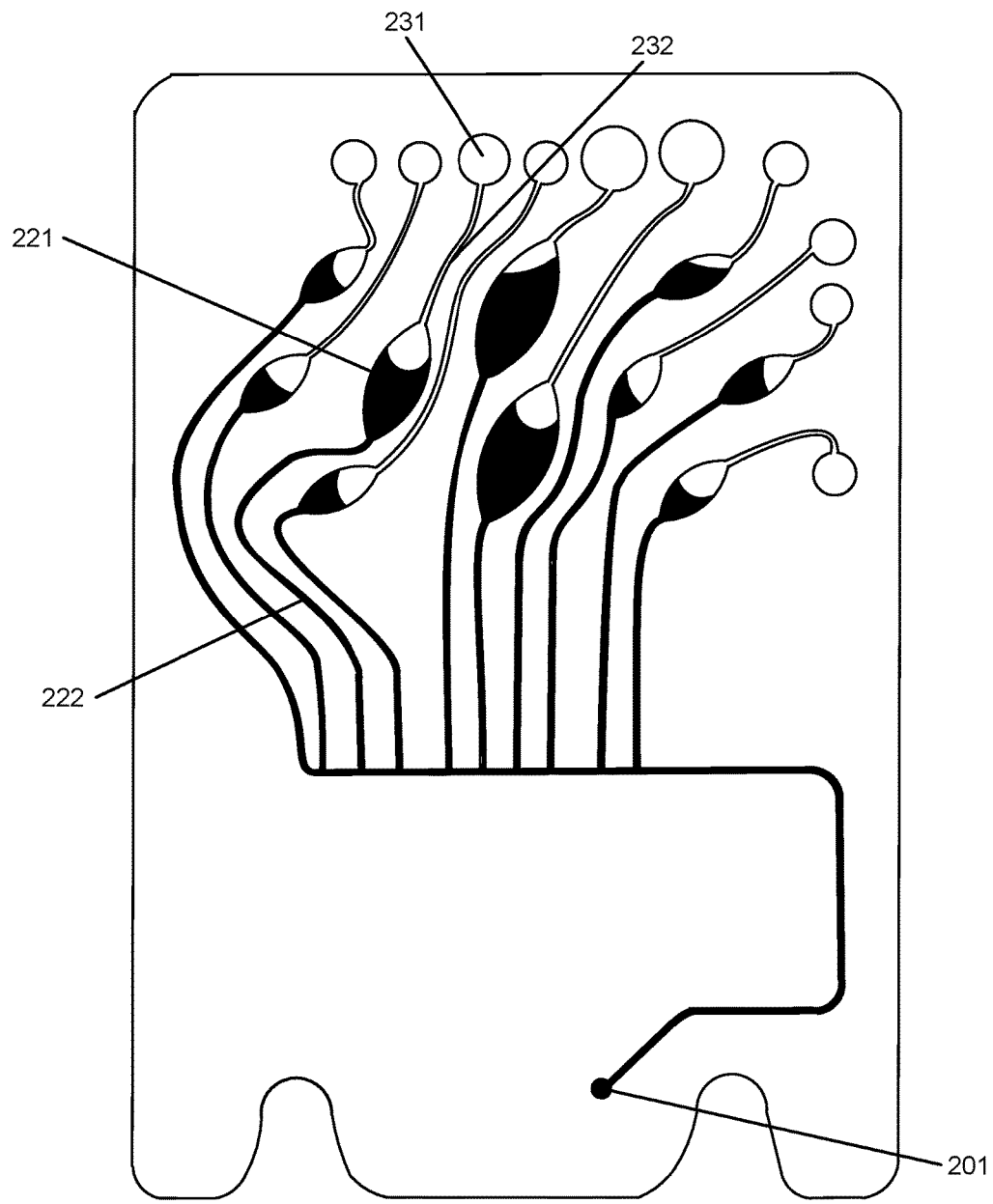
FIG. 2C depicts an apparatus at a time C during simultaneous filling of sample chambers of the apparatus with a fluid sample, in accordance with an embodiment.

As further discussed with regard to FIG. 1, to achieve simultaneous filling of the sample chamber of each fluidic pathway of an apparatus, in some embodiments, the proportionality between the fluid volume of the fluidic pathway and the pneumatic volume of a fluidic pathway is the same for all of the fluidic pathways of the apparatus. Specifically, a ratio of the fluid volume to the pneumatic volume of a fluidic pathway is substantially equivalent for each fluidic pathway of the apparatus. Based on this substantial equivalence between the fluidic pathways, the sample chamber of each fluidic pathway fills at a substantially proportional rate, thereby enabling simultaneous filling of the sample chambers. As referred to herein, "substantially proportional" means that the rates at which the sample chambers fill differ by no more than +/−10% This phenomenon can also be seen in FIG. 2C. Specifically, as seen in FIG. 2C, at the time C, the same proportion of the sample chamber of each fluidic pathway is filled with the fluid sample. This simultaneous filling of the sample chambers occurs not only at the time C, but throughout the filling of the sample chambers as discussed in more detail below with regard to FIGS. 2C and 2D.

FIG. 2C depicts the apparatus 200 at a time C that is subsequent to the time B. At the time C, the common fluid source 201 continues to supply the fluid sample 260 to the fluidic pathways at a supply pressure that is greater than the internal pressure within the fluidic pathways. Because the supply pressure of the fluid sample is still greater than the internal pressure within the fluidic pathways, the fluid sample continues to advance into each fluidic pathway toward the air chamber 231 of the fluidic pathway. Specifically, as shown in FIG. 2C, the fluid sample has advanced into the assay chamber 221 of each of the fluidic pathways of the apparatus.

The air trapped within each fluidic pathway is held at a pressure according to the volume in which the air is contained. Specifically, air contained within a smaller volume has a greater pressure than air contained within a relatively larger volume.

Furthermore, the air trapped within each fludic pathway affects a rate of flow of the fluid sample in the fluidic pathway according to the internal pressure of the fluidic pathway that is dependent, at least in part, on the pressure of the trapped air. Specifically, air at a higher pressure decreases a rate of flow of the fluid sample in the fluidic pathway more than air at a relatively lower pressure. Therefore, because air pressure is inversely proportional to the volume in which the air is contained, air contained within a smaller volume decreases a rate of flow of the fluid sample in the fluidic pathway more than air within a larger volume.

In the embodiment of the apparatus shown in FIG. 2C, each fluidic pathway of the apparatus is configured such that the pneumatic volume of the fluidic pathway is proportional to the fluid volume of the fluidic pathway, and a ratio of the fluid volume to the pneumatic volume of a fluidic pathway is substantially equivalent for each fluidic pathway of the apparatus. As a result, the sample chamber of each fluidic pathway fills at a substantially proportional rate, thereby enabling simultaneous filling of the sample chambers of the apparatus.

Figure 2D:
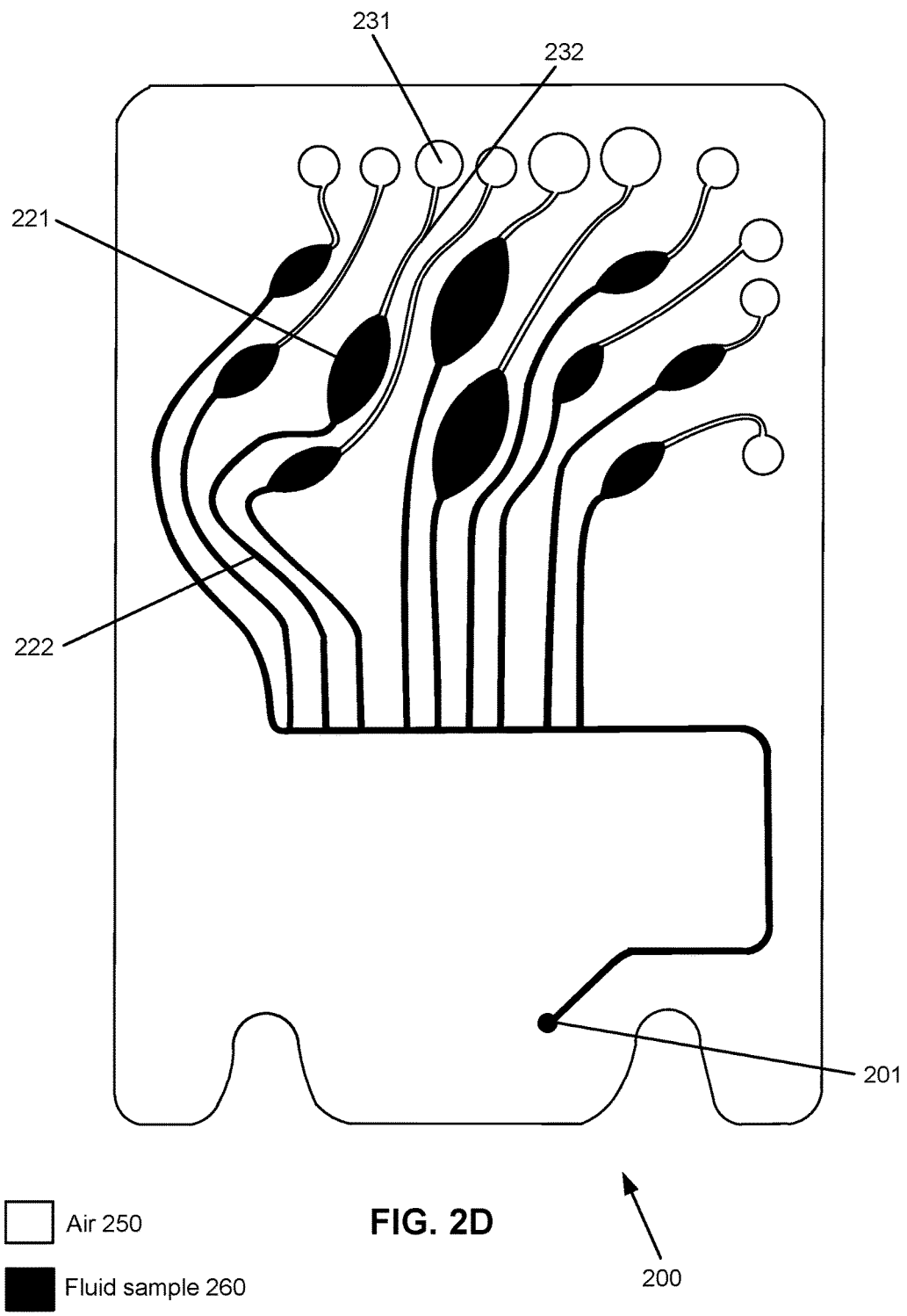
FIG. 2D depicts an apparatus at a time D during simultaneous filling of sample chambers of the apparatus with a fluid sample, in accordance with an embodiment.

FIG. 2D depicts the apparatus 200 at a time D that is subsequent to the time C. At the time D, the common fluid source 201 continues to supply the fluid sample 260 to the fluidic pathways at a supply pressure. However, at the time D, the internal pressure within each fluidic pathway has increased such that the internal pressure within each fluidic pathway equals the supply pressure. Due to this equivalence between the supply pressure and the internal pressure within each fluidic pathway, the fluid sample ceases to advance within the fluidic pathways.

In the embodiment shown in FIG. 2D, the fluid sample stops flowing into each fluidic pathway when the fluid sample has substantially filled the assay chamber 221 of the fluidic pathway. As discussed above, to stop flow of the fluid sample into a fluidic pathway when the assay chamber of the fluidic pathway is substantially filled, the internal pressure within the pneumatic volume and the supply pressure of the fluid sample must be equal when the assay chamber is substantially filled with the fluid sample. To accomplish this, the pneumatic volume of the fluidic pathway, an initial air pressure within the fluidic pathway, and the supply pressure of the fluid sample can be intentionally selected. In this way, the fluid sample can be confined to the assay chambers of the apparatus.

As further shown in FIG. 2D, the assay chamber of each fluidic pathway completes filling at the same time D. In other words, the filling of the sample chambers of FIG. 2D) is simultaneous. As discussed above, this simultaneous filling of the sample chambers is the result of the pneumatic volume of a fluidic pathway being proportional to the fluid volume of the fluidic pathway, and a ratio of the fluid volume to the pneumatic volume of a fluidic pathway being substantially equivalent for each fluidic pathway of the apparatus.

Figure 2E:
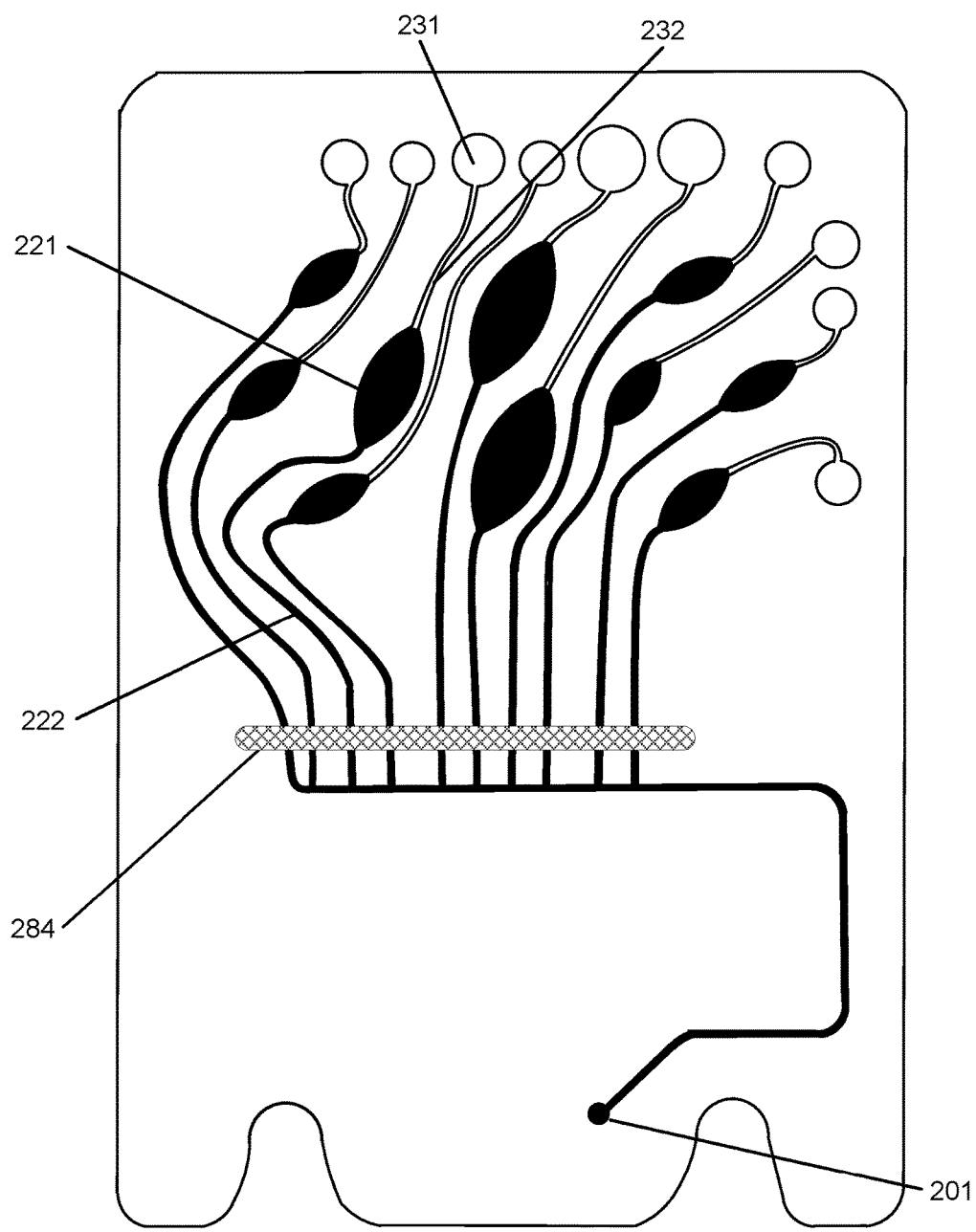
FIG. 2E depicts an apparatus at a time E during simultaneous filling of sample chambers of the apparatus with a fluid sample, in accordance with an embodiment.

FIG. 2E depicts the apparatus 200 at a time F that is subsequent to the time D. At the time E, the fluid sample 260 has stopped flowing into the fluidic pathways, and the sample chamber of each fluidic pathway is substantially filled. The level of the fluid sample within each fluidic pathway is maintained by the equilibrium between the supply pressure of the fluid sample and the internal pressure within the pneumatic compartment of the fluidic pathway.

To maintain this level of the fluid sample within each fluidic pathway without continued application of the supply pressure by the common fluid source 201, a portion of the entry conduit 222 of each fluidic pathway can be sealed. One acceptable method of sealing the entry conduits is heat staking with a heated element 284 such that the fluidic pathway is sealed off from the common fluid source. Note that the supply pressure of the fluid sample is maintained during the heat staking process as shown in FIG. 2E.

In some embodiments, a first film is adhered to a surface of at least a portion of the apparatus, such that the first film forms one wall of the entry conduit of each fluidic pathway. In one implementation the first film has a similar melting point as the substrate of the apparatus.

In further embodiments, a second film is adhered to the first film. In such embodiments, the second film has a higher melting point than the first film and the surface of the apparatus such that when heat is applied to the apparatus via the heated element to heat stake the entry conduit of each fluidic pathway, the first film and the surface of the apparatus melt prior to the second film. This higher melting point of the second film prevents the pressurized fluid sample from escaping from the fluidic pathways as the first film and the surface of the apparatus are melted. The result of this heat staking process is a melted first film, which forms a heat stake 203 as depicted in FIG. 2F.

The sealing process renders each fluidic pathway a completely closed system from which matter cannot travel in or out, and for which, devoid of any changing variables, the internal pressure within each fluidic pathway remains constant.

In embodiments in which the assay chamber of each fluidic pathway is configured to contain an assay, sealing the entry conduits is beneficial because it isolates the fluidic pathway from the environment such that the assay can be performed in an enclosed and controlled volume without contamination across fluidic pathways or to the environment. Furthermore, the constant internal pressure locked into the fluidic pathway by the heat staking minimizes the formation of bubbles within the assay chambers during actuation of the assay.

Figure 2F:
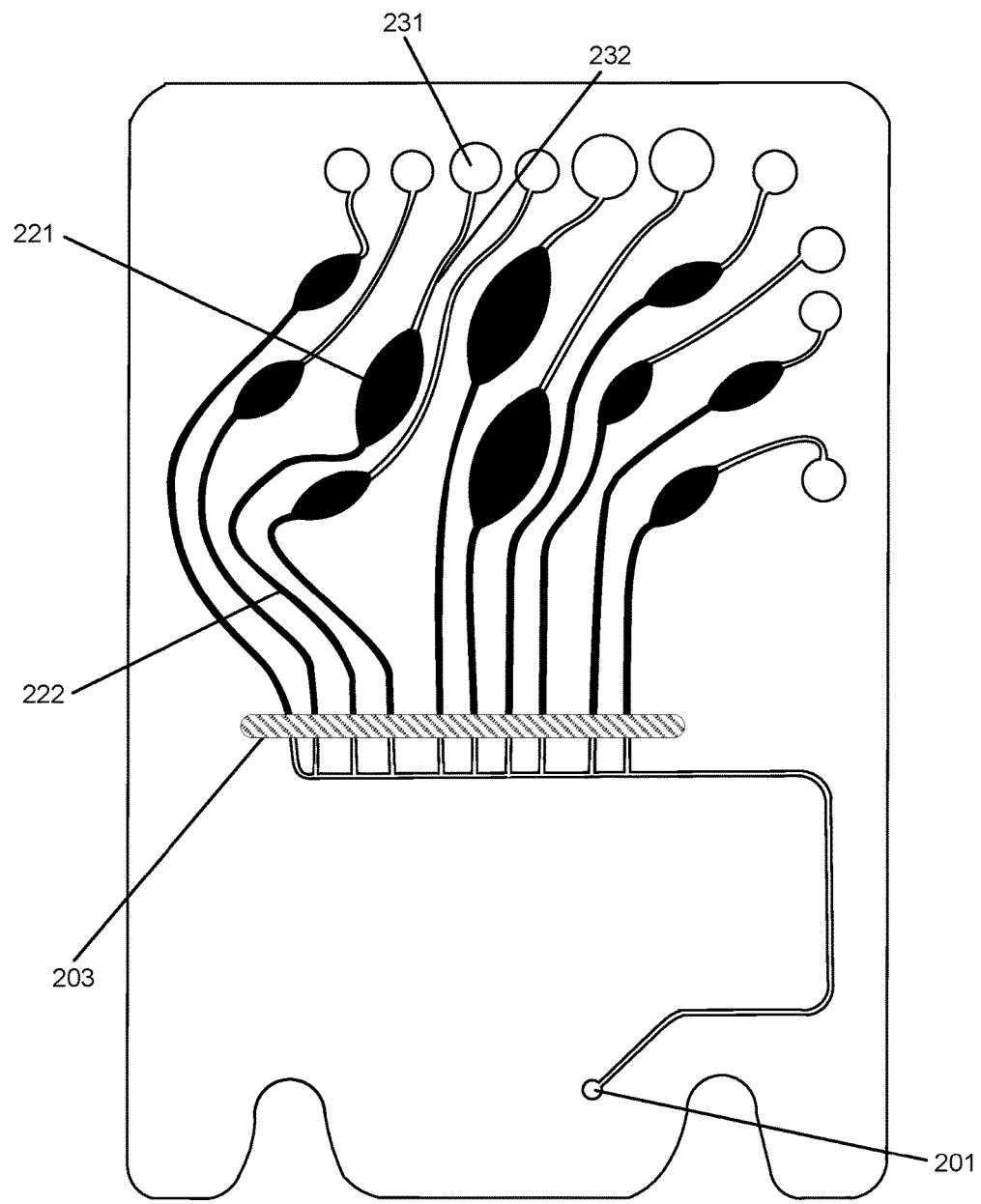
FIG. 2F depicts an apparatus at a time F during simultaneous filling of sample chambers of the apparatus with a fluid sample, m accordance with an embodiment.

FIG. 2F depicts the apparatus 200 at a time F that is subsequent to the time E. At the time F, the heat staking process is complete, and the heat stake 203 is in place such each fluidic pathway is sealed off from the common fluid source 201. As a result of the heat staking, internal pressure within each fluidic pathway remains constant such that the level of the fluid sample is maintained within each fluidic pathway without the assistance of the supply pressure from the common fluid source. Accordingly, as shown in FIG. 2F, the supply pressure from the common fluid source is released. At this stage, the apparatus is prepared for use in one or more assays.

Devices

Figure 3A:
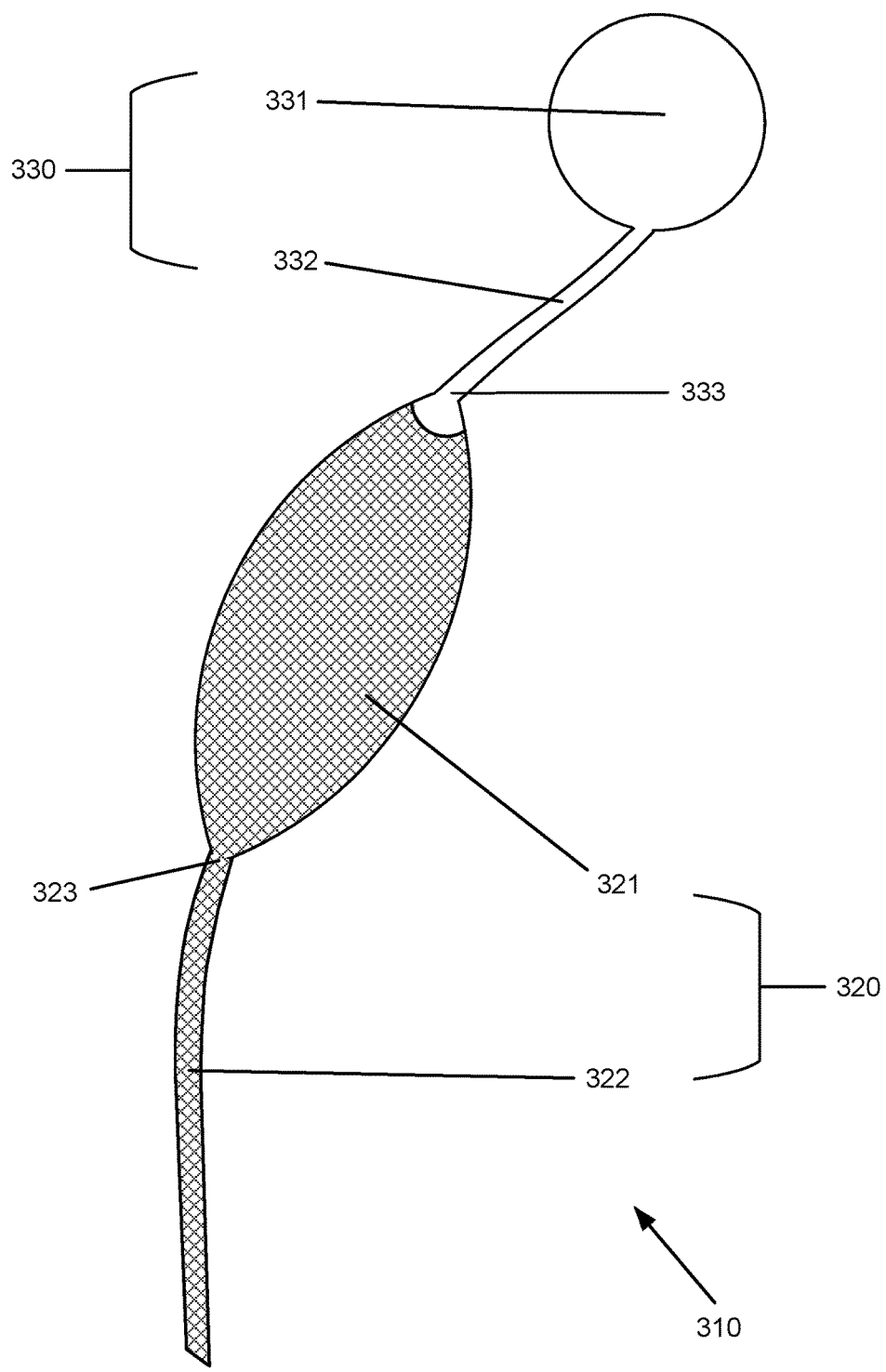
FIG. 3A is an Illustration of an independent fluidic pathway, in accordance with an embodiment.

FIG. 3A is an illustration of an independent fluidic pathway 310, in accordance with an embodiment. The independent fluidic pathway comprises a sample chamber 320 and a pneumatic compartment 330. The sample chamber comprises an entry conduit 322 and an assay chamber 221. The sample chamber comprises a fluid volume. The pneumatic compartment comprises a pneumatic conduit 332 and an air chamber 331. The pneumatic compartment comprises a pneumatic volume.

The fluid volume and the pneumatic volume of the fluidic pathway are configured to contain air 350 and/or a fluid sample 360. As shown in FIG. 3A, air is denoted within the fluidic pathway by white space. Contrastingly, the fluid sample is denoted within the fluidic pathway by a crosshatch pattern.

In the embodiment shown n in FIG. 3A, the fluid volume is substantially filled with the fluid sample, and the pneumatic volume is filled with air. However, in alternative embodiments, the fluid volume and the pneumatic volume may be filled with any ratio of the fluid sample and/or air.

For example, prior to introduction of the fluid sample to the fluidic pathway, the entire fluidic pathway can be filled with air. The process by which a fluidic pathway is filled with the fluid sample is discussed in detail below with regard to FIGS. 2A-2F.

The entry conduit of the fluidic pathway is configured to transport the fluid sample from a common fluid source into the assay chamber of the fluidic pathway. A portion of the entry conduit that connects the entry conduit to the assay chamber is referred to as an entry conduit terminus 323.

The assay chamber is configured to contain an assay. In some embodiments, the assay chamber may include features to facilitate the assay. For example, as discussed in further detail below with regard to FIG. 3B, the assay chamber is configured to minimize formation of bubbles during transmission of the fluid sample into the assay chamber.

The pneumatic conduit connects the assay chamber to the air chamber of the fluidic pathway. A portion of the pneumatic conduit that connects the pneumatic conduit to the assay chamber is referred to as a pneumatic compartment terminus 333.

As described below with regard to FIG. 1, the pneumatic compartment is configured to control the rate flow of a fluid sample into the assay chamber of the fluidic pathway according to an internal pressure within the pneumatic compartment.

The independent fluidic pathway is a continuous system. Specifically, the entry conduit is connected to, and in fluidic communication with, the assay chamber. The assay chamber is connected to, and in fluidic communication with, the pneumatic conduit. The pneumatic conduit is connected to, and in fluidic communication with, the air chamber.

As a result of the continuity of the independent fluidic pathway, a fluid sample can travel throughout the fluidic pathway. Specifically a fluid sample can travel through the entry conduit, into the assay chamber, through the pneumatic conduit, and into the air chamber of each fluidic pathway.

Excluding an opening at one end of the entry conduit, the independent fluidic pathway is a closed system. In other words, matter contained within the fluidic pathway cannot travel into or out of the fluidic pathway, except via the one opening of the entry conduit. Therefore, by sealing off the one opening of the entry conduit, the fluidic pathway becomes a completely closed system from which matter cannot travel in or out, and for which, devoid of any changing variables, internal pressure within the fluidic pathway remains constant.

Figure 3B:
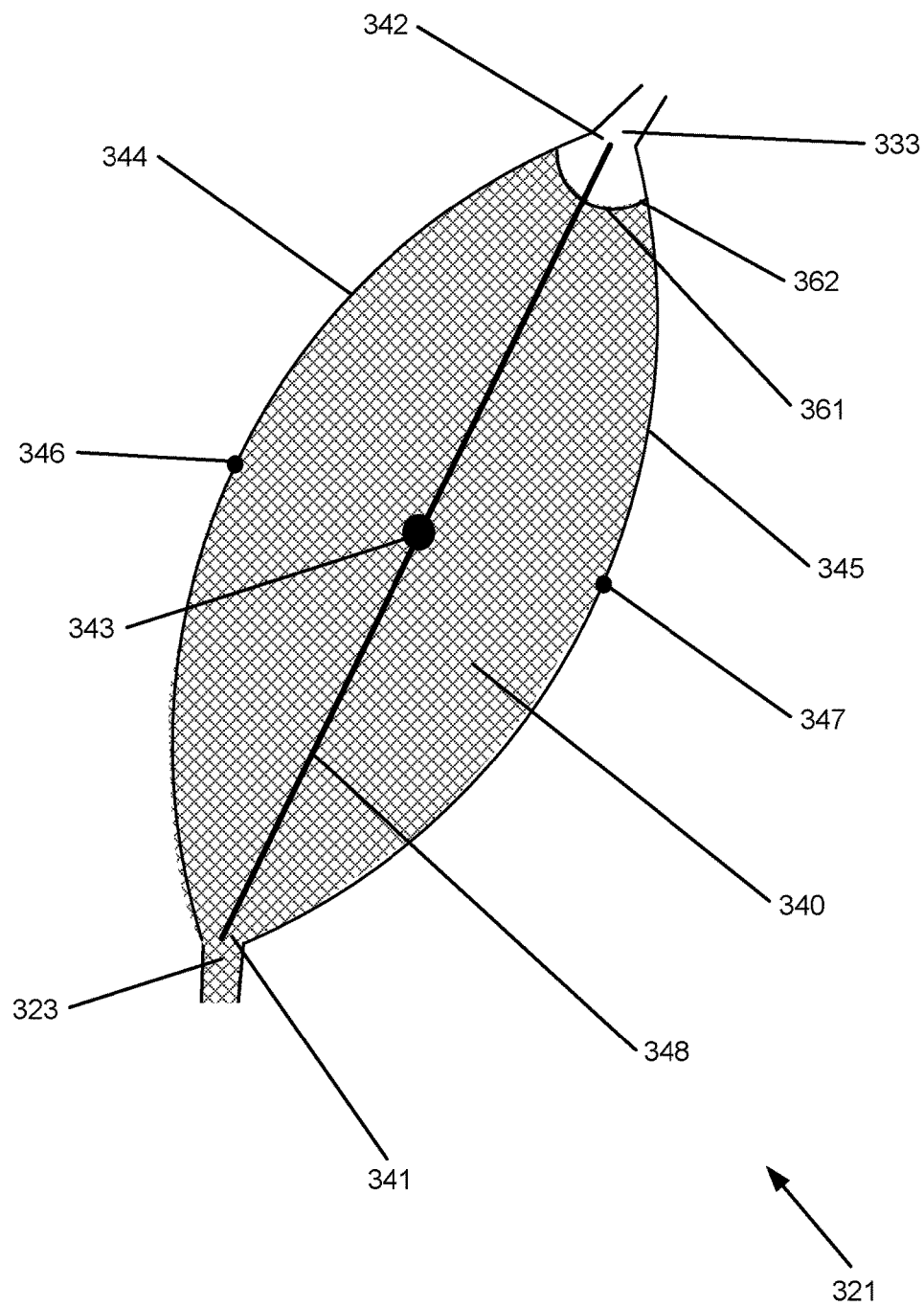
FIG. 3B is an illustration of an assay chamber, in accordance with an embodiment.

FIG. 3B is an illustration of an assay chamber 321, in accordance with an embodiment. The assay chamber comprises an assay chamber volume. In some embodiments, assay chamber volume is between 1 μL and 35 μL.

As shown in the legend at the bottom left-hand corner of FIG. 3B, air 350 is denoted within the assay chamber volume by white space. Contrastingly, a fluid sample 360 is denoted within the assay chamber volume by a crosshatch pattern. In the embodiment of the assay chamber depicted in FIG. 3B, the sample chamber is substantially filled with the fluid sample. In other words, at least 90% of the volume of the sample chamber contains the fluid sample, and at most 10% of the pneumatic compartment contains the fluid sample.

As described above with regard to FIG. 1, in some embodiments, the assay chamber is configured to contain an assay. In such embodiments, the assay chamber may include features to facilitate the assay. For example, in the embodiment of the assay chamber depicted in FIG. 3B, the assay chamber is configured to minimize formation of bubbles during transmission of the fluid sample into the assay chamber. This feature is advantageous during assay actuation because bubbles alter the effective volume of the assay chamber and can interfere with the results of the assay.

In the embodiment shown in FIG. 3B, to minimize formation of bubbles during transmission of the fluid sample into the assay chamber, the assay chamber comprises a doubled tapered chamber 340. The role of the double tapered chamber in minimizing bubble formation is discussed in greater detail below. The double tapered chamber comprises a tapered inlet 341, a tapered outlet 342, a first curved boundary 344, and a second curved boundary 345.

The tapered inlet is an inlet of the double tapered chamber that is configured to receive a fluid sample from an entry conduit. Specifically, the tapered inlet is connected to, and in fluidic communication with, the entry conduit via an entry conduit terminus 323. As noted above, the entry conduit terminus is a portion of the entry conduit that connects the entry conduit to the assay chamber. Therefore, to receive a fluid sample in the double tapered chamber, the fluid sample travels through the entry conduit terminus and into the double tapered chamber via the tapered inlet.

The tapered outlet is an outlet of the double tapered chamber that is connected to, an in fluidic communication with, a pneumatic compartment via a pneumatic compartment terminus 333. As noted above, the pneumatic compartment terminus is a portion of a pneumatic conduit of the pneumatic compartment that connects the pneumatic compartment to the assay chamber. The tapered inlet and the tapered outlet are separated by a largest dimension 348 of the assay chamber volume.

In embodiments in which the double tapered chamber is substantially filled with the fluid sample, as shown in FIG. 3B, air may be contained within the pneumatic compartment, including within the pneumatic compartment terminus. In such embodiments, the tapered outlet can serve to connect the fluid sample located within the double tapered chamber and the air located within the pneumatic compartment, such that the fluid sample can interface with the air. This interface between the fluid sample and the air can be used to control a rate of flow of the fluid sample, as discussed in detail above with regard to FIGS. 1-2D.

The double tapered chamber comprises two curved boundaries, the first curved boundary and the second curved boundary. Each curved boundary extends from the tapered inlet to the tapered outlet such that the two curved boundaries enclose the assay chamber volume. Therefore, the only pathways in or out of the double tapered chamber are via the tapered inlet and the tapered outlet, as described above.

Each curved boundary of the double tapered chamber comprises a midpoint. Specifically, the first curved boundary comprises a first curved boundary midpoint 346 and the second curved boundary comprises a second curved boundary midpoint 347. A distance between the two curved boundaries decreases as the boundaries curve from the midpoint toward the tapered inlet and from the midpoint toward the tapered outlet. In other words, each curved boundary is concave with regard to a center point 343 of the assay chamber volume. In some embodiments, this gradual decrease in the distance between the two curved boundaries as the boundaries curve from their midpoints toward the tapered inlet and the tapered outlet of the assay double tapered chamber, occurs at the same rate towards both the tapered inlet and the tapered outlet, such that curved boundary is symmetric about the midpoint of the curved boundary. In further embodiments, this gradual decrease in the distance between the two curved boundaries as the boundaries curve from their midpoints toward the tapered inlet and the tapered outlet of the assay double tapered chamber, occurs at the same rate towards both the tapered inlet and the tapered outlet for both the first curved boundary and the second curved boundary, such that two curved boundaries are symmetric to one another about the largest dimension of the assay chamber volume.

As mentioned above, the configuration of the assay chamber as the double tapered chamber shown in FIG. 3B minimizes the formation of bubbles during transmission of the fluid sample into the assay chamber. Specifically, as the fluid sample flows into the double tapered chamber, the interface between the fluid sample and the air within the double tapered chamber comprises a meniscus 361. The meniscus of the fluid sample includes a leading front 362. The leading front of the meniscus is a portion of the meniscus that leads the advance of the fluid sample within the assay chamber. In embodiments in which the fluid sample substantially fills the assay chamber, such as the embodiment depicted in FIG. 3B, the leading front of the meniscus is a portion of the meniscus that is in closest proximity to the tapered outlet.

To minimize formation of bubbles during transmission of the fluid sample into the assay chamber, as the fluid sample flows into the double tapered chamber, the two curved boundaries of the double tapered chamber slow the rate of advance of the fluid sample at the leading front of the meniscus of the fluid sample, such that when the fluid sample reaches the tapered outlet, the meniscus of the fluid sample is substantially symmetric with respect to the largest dimension of the assay chamber. As used herein, "substantially symmetric" means that at the point that the leading front of the meniscus of the fluid sample reaches the tapered outlet, the trailing front of the meniscus is has progressed at least half of the distance from the midpoint of the curved boundary to the tapered outlet. Ensuring that the meniscus of the fluid sample is substantially symmetric with respect to the largest dimension of the assay chamber volume by the time the fluid sample reaches the tapered outlet, minimizes the trapping of bubbles within the assay chamber during filling.

Figure 4:
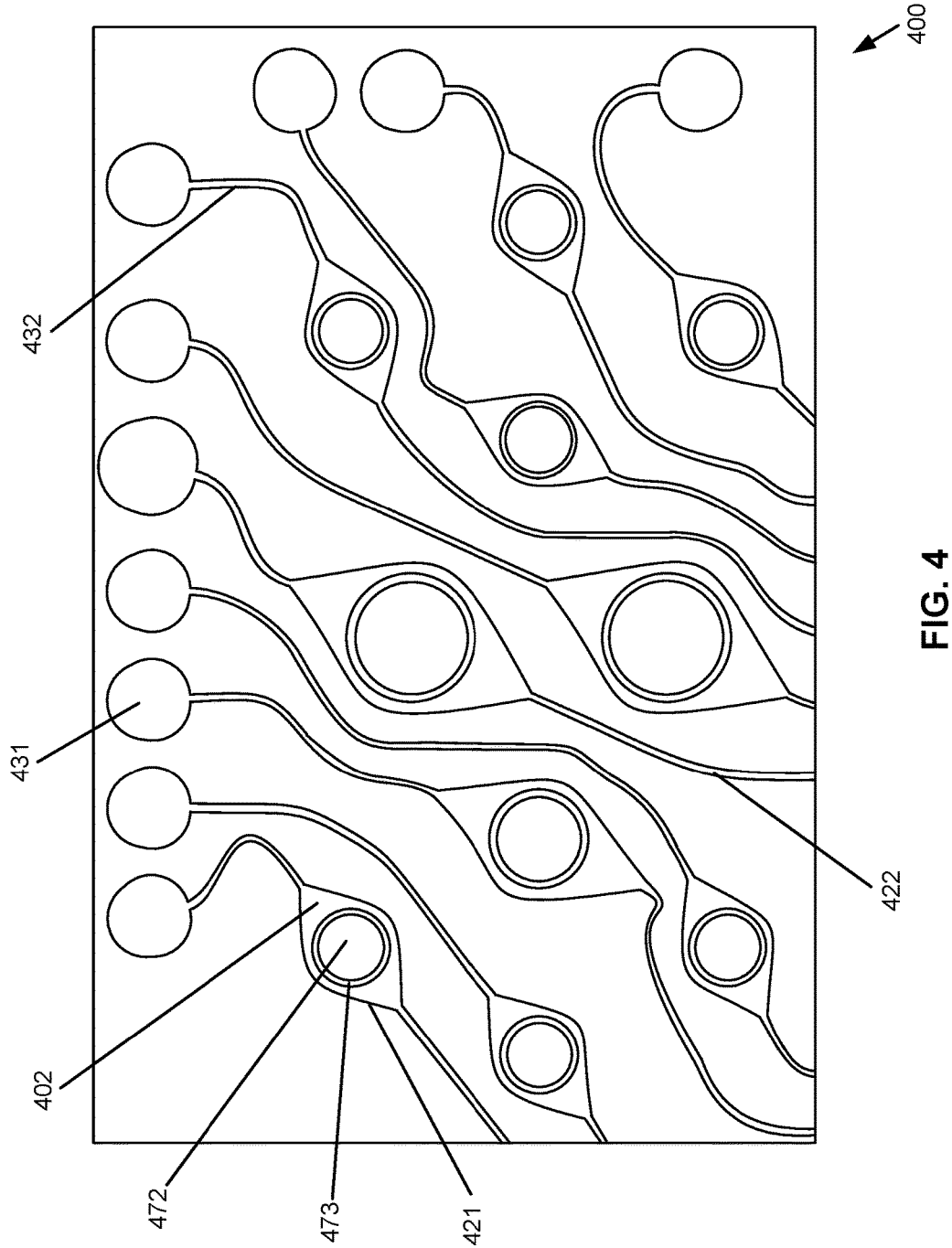
FIG. 4 is an illustration of a portion of an apparatus for transmitting a fluid sample from a fluid source into multiple sample chambers, in accordance with an embodiment.

FIG. 4 is an illustration of a portion of an apparatus 400, in accordance with an embodiment. Similar to the embodiments of the apparatuses discussed above with regard to FIGS. 1-3A, the apparatus depicted in FIG. 4 comprises a plurality of fluidic pathways. Furthermore, each fluidic pathway is a continuous, independent fluidic pathway that includes an entry conduit 422, an assay chamber 421, a pneumatic conduit 432, and an air chamber 431. The common fluid source and each fluidic pathway's attachment thereto has been cropped from the illustration of FIG. 4.

As noted above with regard to FIGS. 1 and 3A, excluding a connection between a common fluid source and the entry conduit of a fluidic pathway, each fluidic pathway is a closed system. In some embodiments, to configure a fluidic pathway to be a closed system, the fluidic pathway comprises one or more bounding surfaces. For example, as discussed above with regard to FIGS. 2E and 2F, a bounding surface of each entry conduit of the apparatus may be a first film and/or a second film.

In the embodiment of the apparatus shown in FIG. 4, the assay chamber of each fluidic pathway comprises two bounding surfaces, such that the assay chamber is an enclosed system except for a connection of the assay chamber to the entry conduit and a connection of the assay chamber to the pneumatic conduit. Specifically, as shown in FIG. 4, the assay chamber of each fluidic pathway comprises a first bounding surface formed in a monolithic substrate 402, and a second bounding surface formed by a plug cap 472. The plug cap is a portion of a plug (labeled in FIGS. 6A-7) that protrudes into the monolithic substrate at a depth. The plug is placed within an opening of the monolithic substrate. Together, the monolithic substrate and the plug cap form a continuous bounding surface of the assay chamber.

In some implementations, each assay chamber further comprises a third bounding surface that is formed by a film. In such implementations, together, the monolithic substrate, the plug, and the film enclose the assay chamber volume.

In certain embodiments, as shown in FIGS. 4-7, the plug cap includes a flange 473. The flange comprises a projecting rim of the plug cap that can be welded and/or adhered to a surface of the assay chamber, thereby stabilizing the position of the plug within the opening of the monolithic substrate of the assay chamber such that the plug is not ejected from the opening during pressurization of contents within the assay chamber. The configurations of the monolithic substrate and the plug cap are discussed in further detail below with regard to FIGS. 5-6B.

Figure 5:
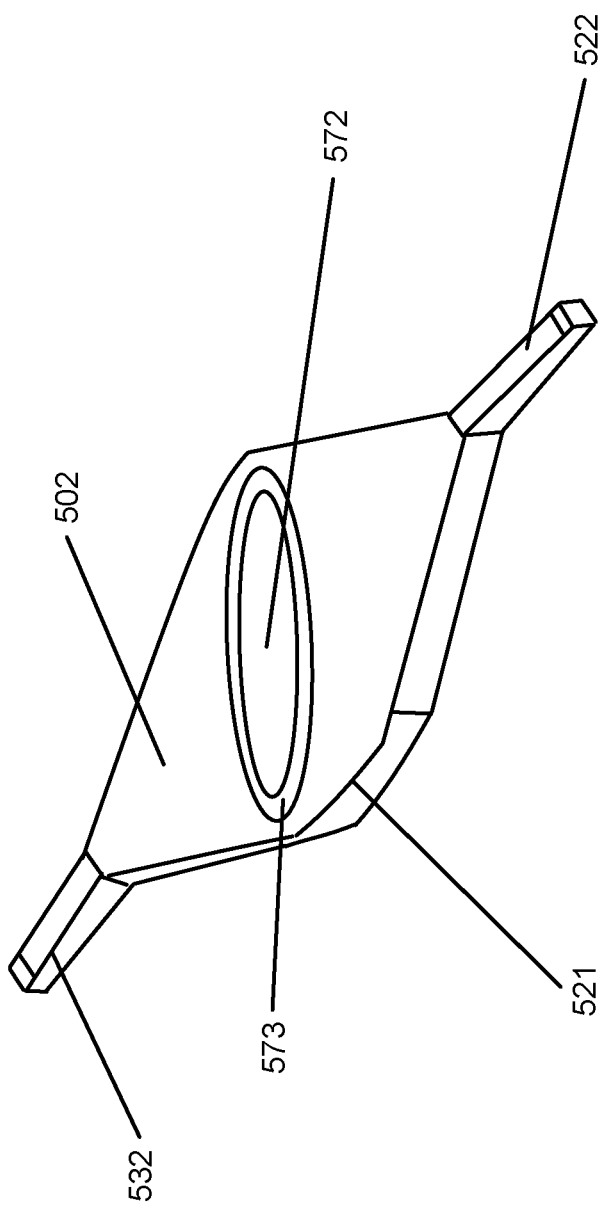
FIG. 5 is a three-dimensional illustration of an assay chamber, in accordance with an embodiment.

FIG. 5 is a three-dimensional illustration of an assay chamber 521, in accordance with an embodiment. As discussed in detail above, the assay chamber is connected to, and is in fluidic communication with, both an entry conduit 522, and a pneumatic conduit 532. Additionally, the assay chamber is bounded by a monolithic substrate 502 and a plug cap 572.

In a preferred implementation, the monolithic substrate of the assay chamber is a single structural component. In some embodiments, the monolithic substrate is injection molded. In some embodiments, such as the embodiment depicted in FIG. 5, the monolithic substrate may form a portion or all of a double tapered chamber, as discussed above with regard to FIG. 3B. Specifically, the monolithic substrate may form the two curved boundaries of the double tapered chamber, as discussed above with regard to FIG. 3B.

Figures 6A, 6B:
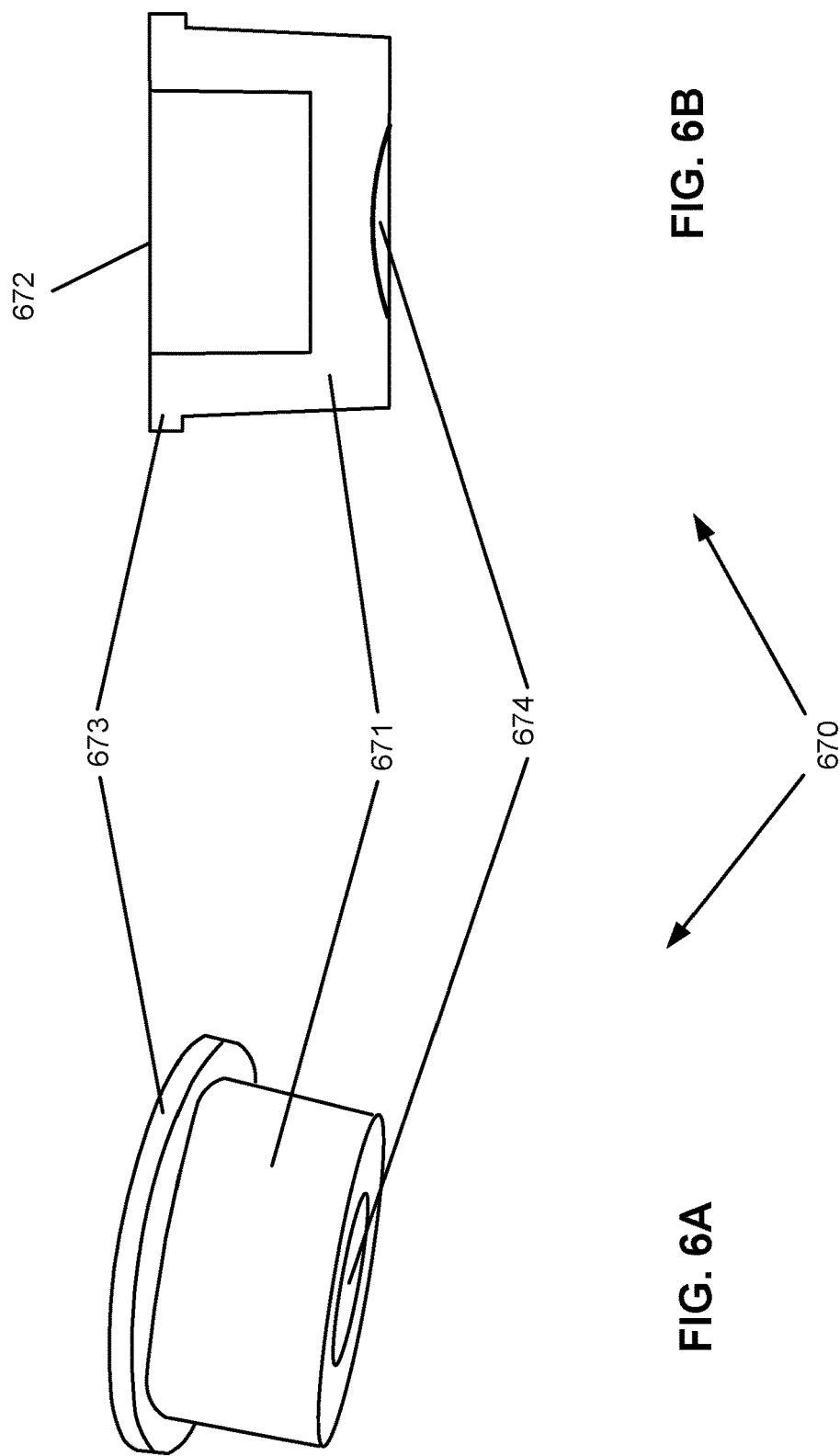
FIG. 6A is a three-dimensional illustration of a plug, in accordance with an embodiment.
FIG. 6B is a cross-sectional illustration of a plug, in accordance with an embodiment.
Figure 7:
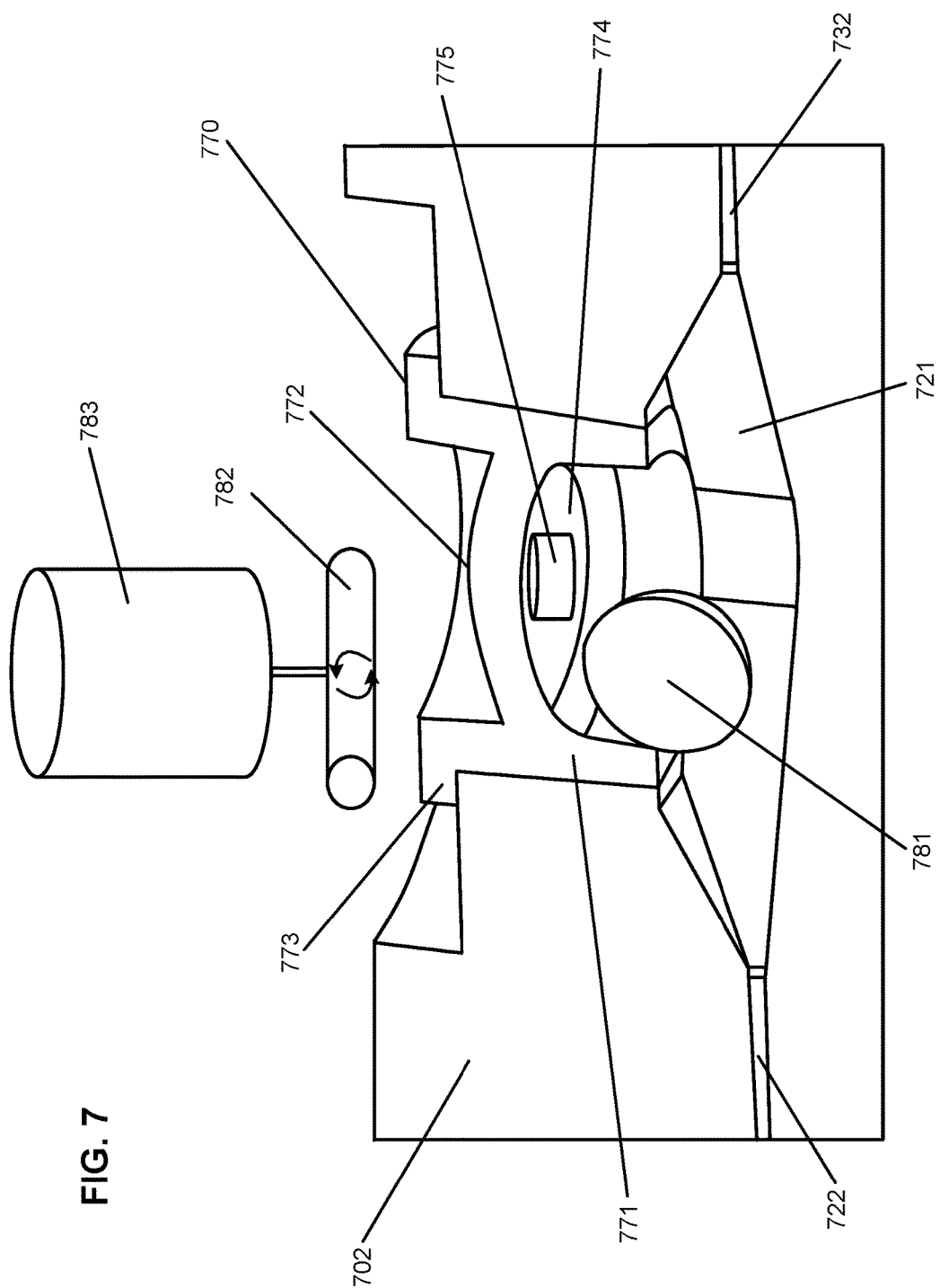
FIG. 7 is a three-dimensional, cross-sectional illustration of an assay chamber, in accordance with an embodiment.

As mentioned above with regard to FIG. 4, the plug cap is a component of a plug (labeled in FIGS. 6A-7). As also noted above, in some embodiments, the plug cap includes a flange 573 that can be welded and/or adhered to a surface of the assay chamber to stabilize the position of the plug within the opening of the monolithic substrate of the assay chamber. The plug protrudes into the monolithic substrate at a depth such that the component of the plug that is visible on the exterior of the assay chamber is the plug cap. In embodiments in which the plug cap includes a flange, the flange is also visible on the exterior of the assay chamber as shown in FIGS. 4 and 5. In some embodiments, such as embodiments in which the assay chamber is used to contain an assay, the plug is transparent such that the assay within the assay chamber is optically detectable from outside of the assay chamber.

FIG. 6A is a three-dimensional illustration of a plug 670, in accordance with an embodiment. The plug comprises a plug cap 672 and a plug body. In some embodiments, such as the embodiment shown in FIG. 6A, the plug cap also includes a flange 673. In further embodiments, such as the embodiment shown in FIG. 6A, the plug cap also includes an internal cavity 674, discussed in further detail below.

In some embodiments, such as the embodiments shown in FIGS. 4 and 5, the plug comprises a bounding surface of an assay chamber. Specifically, the plug can be placed within an opening of a monolithic substrate of the assay chamber such that the plug cap forms a bounding surface of the assay chamber and the plug body protrudes into the monolithic substrate, and also into the assay chamber, at a depth. In some embodiments, a volume of the assay chamber depends at least in part on the depth at which the plug body protrudes into the monolithic substrate to form a bounding surface of the assay chamber. Specifically, the greater the depth that the plug body protrudes into the assay chamber, the smaller the volume of the assay chamber.

As noted above, in some embodiments, the plug cap includes the flange shown in FIG. 6A. The flange can be welded and/or adhered to a surface of the assay chamber to stabilize the position of the plug within the opening of the monolithic substrate of the assay chamber.

As also noted above, in certain implementations, the plug cap may include the internal cavity, as shown in FIG. 6A. The surface of the cap, including the optional internal cavity, is in fluidic communication with the assay chamber. In certain embodiments, particularly in embodiments which an assay chamber is used to contain an assay, the internal cavity of the plug body may contain one or more dried reagents (labeled in FIG. 7). In such embodiments, the assay chamber can be used to re-hydrate and/or solubilize the one or more dried reagents, as discussed in further detail below with regard to FIG. 7.

FIG. 6B is a cross-sectional illustration of the plug 670, in accordance with an embodiment.

FIG. 7 is a three-dimensional, cross-sectional illustration of an assay chamber 721, in accordance with an embodiment. As described above, the assay chamber is connected to, and in fluidic communication with, both an entry conduit 722 and a pneumatic conduit 732. Also as described above, the assay chamber is bounded by a monolithic substrate 702 and a plug 770. In particular, the plug is fixed within an opening in the monolithic substrate such that a plug body 771 protrudes into monolithic substrate at a depth, and a plug cap 772 forms a bounding surface of the assay chamber. A volume of the assay chamber depends, in part, on the depth at which the plug body protrudes into the monolithic substrate. In further embodiments, the assay chamber can also be bounded by a film.

As discussed above, the assay chamber may include features to facilitate an assay. For instance, in some embodiments, the plug is transparent such that an interior of the assay chamber is optically detectable from outside of the assay chamber. As noted above, in some embodiments, the plug cap includes a flange 773. The flange can be welded and/or adhered to a surface of the assay chamber to stabilize the position of the plug within the opening of the monolithic substrate of the assay chamber. As also noted above, in certain implementations, the plug cap includes an internal cavity 774. In some embodiments, the internal cavity of the plug cap may contain dried reagents 775 for use in an assay. The dried reagents can be rehydrated and/or solubilized by a fluid sample that enters the assay chamber via the entry conduit as discussed above.

To decrease the amount of time required to rehydrate and/or solubilize the dried reagents, the interior of the assay chamber may contain a magnetic mixing element 781 that is capable of gyration. Gyration of the magnetic mixing element can aid in mixing contents contained within the assay chamber, and therefore can aid in rehydrating and/or solubilizing the dried reagents. In some embodiments, the magnetic mixing element may be spherical in shape. In alternative embodiments, the magnetic mixing element may comprise any alternative shape.

To drive gyration of the magnetic mixing element within the assay chamber, an exterior magnet 782 that is capable of rotation may be located exterior to the assay chamber. To drive rotation of the exterior magnet such that the exterior magnet induces gyration of the magnetic mixing element, in some embodiments the exterior magnet may be mechanically coupled to a motor 783 capable of driving rotation of the exterior magnet. By rotating the exterior magnet, gyration of the magnetic mixing element within the assay chamber is induced.

In embodiments in which the exterior magnet is located above a center of the assay chamber, the exterior magnet may induce balanced spinning of the magnetic mixing element within the assay chamber. Balanced spinning is ineffective in mixing contents. Therefore, to avoid balanced spinning of the magnetic mixing element such that contents contained within the assay chamber are more effectively mixed, in some embodiments, such as the embodiments shown in FIG. 7, the exterior magnet is located off-center of the assay chamber. By locating the exterior magnet off-center of the assay chamber, the magnetic mixing element does not rotate in a perfectly balanced fashion within the center of the assay chamber, but rather moves around the assay chamber in a gyrating motion. This more effectively mixes contents contained within the assay chamber.

EXAMPLES

Several separate experiments were performed to determine operational ranges of the magnetic mixing element described above with regard to FIG. 7.

Example 1: Unidirectional Mixing

A first experiment involved rehydrating dried reagents using unidirectional gyration in a device as illustrated in FIG. 7 for 60 seconds at 1,030 rpm and 2,060 rpm. Additional dried reagents were rehydrated using a standard laboratory benchtop protocol for use as a positive control. These rehydrated reagents were used to amplify nucleic acid sequences using LAMP. The performance of the positive control was used as a baseline to which the results of the two device rehydration conditions were compared.

The results of the first experiment are depicted below in Table 1. Considering the standard deviation of the Time-to-Positive (Tp) and the percentage of reactions that resulted in amplification, the experiment results demonstrate that 1,030 rpm is insufficient to rehydrate dried reagents when utilizing unidirectional gyration for 60 seconds. Increasing the gyration speed to 2,060 rpm decreases the standard deviation and results in 100% amplification, suggesting increased gyration speed is necessary for unidirectional mixing.

TABLE 1

| Condition | Average Tp (min) | Std Dev (min) | Reactions that Amplified |
|---|---|---|---|
| Device-1,030 rpm gyration (n = 3) | 15.0 | 4.04 | 83% |
| Device-2,060 rpm gyration (n = 3) | 10.9 | 2.11 | 100% |
| Positive Controls (n = 4) | 10.0 | 0.29 | 100% |

Example 2: Alternating Gyration Low Speed

A second experiment—performed in two separate parts—involved alternating the gyration direction every 15 seconds for 60 seconds using a gyration speed of 1,030 rpm. Additional dried reagents were rehydrated using a standard laboratory benchtop protocol for use as a positive control.

These rehydrated reagents were used to amplify nucleic acid sequences using LAMP. The performance of the positive control was used as a baseline to which the results of the device rehydration condition were compared.

The results of the second experiment are depicted below in Table 2. In comparison to the results of 1,030 rpm unidirectional gyration in the Example 1, these results demonstrate that alternating the gyration direction every 15 seconds improves the rehydration performance of the device and permits a lower gyration speed to be employed.

TABLE 2

| Condition | Average Tp (min) | Std Dev (min) | Reactions that Amplified |
|---|---|---|---|
| Device-1,030 rpm gyration (n = 3) | 9.7 | 0.33 | 100% |
| Positive Controls (n = 6) | 9.4 | 0.74 | 100% |

Example 3: Alternating Gyration Medium Speed

A third experiment involved alternating the gyration direction every 15 seconds for 60 seconds using a gyration speed of 2,060 rpm. The remainder of the protocol was identical to the second experiment.

The results of the third experiment are depicted below in Table 3. In contrast to the results of 2,060 rpm unidirectional gyration in Example 1, these results demonstrate that alternating the gyration direction every 15 seconds improves the device's rehydration performance even at 2,060 rpm by reducing the standard deviation of the rehydrated reagents Time-to-Positive. These results further indicate that the increased shear caused by alternating the gyration direction does not noticeably damage the rehydrated enzyme.

TABLE 3

| Condition | Average Tp (min) | Std Dev (min) | Reactions that Amplified |
|---|---|---|---|
| 2,060 rpm, alternating gyration directions (n = 3) | 9.49 | 0.633 | 100% |
| Positive Controls (n = 4) | 8.88 | 0.304 | 100% |

The extent of rehydration of dried reagents rehydrated with the device using 2,060 rpm alternating gyration for 60 seconds was compared to controls rehydrated using the standard laboratory benchtop protocol. Concentration of the resulting solutions was quantified against a standard curve using a spectrophotometer. The results of the fourth experiment are depicted below in Table 4. These results further demonstrate that the device is capable of matching the rehydration performance of the standard benchtop protocol

TABLE 4

| Condition | Percent of 1x Concentration | Std Dev |
|---|---|---|
| Device (n = 4) | 82.2% | 2.2% |
| Controls (n = 2) | 91.0% | 1.8% |

Example 4: Extended Alternating Gyration

A fourth experiment involved unidirectional gyration at 2,060 rpm for 30 seconds and 45 seconds rather than the 60 second duration used by the three proceeding experiments. The remainder of the protocol was identical to that described in Example 2 and Example 3

The results of the fourth experiment are depicted below in Table 5. These results demonstrate that the device is capable of rehydrating dried reagents to an acceptable degree in fewer than 60 seconds. Incorporating the results of Example 2, the addition of alternating gyration direction has the potential to further strengthen this capability.

TABLE 5

| Sample | Average $T_p$ | Std Dev $T_p$ |
|---|---|---|
| 45 seconds | 10.27 | 0.712 |
| 30 seconds | 10.01 | 0.390 |
| Dry down control (n = 4) | 9.23 | 0.327 |

Example 5: No Loss of Nucleic Acid

To confirm that no nucleic acid is lost by virtue of mixing within a device as described in FIGS. 1-7, a known concentration of nucleic acid target was loaded into the device without the presence of dried reagents for 60 seconds with 2,060 rpm alternating gyration and no gyration. The concentration of resulting nucleic acid solutions were compared to the original input solution via RT-qPCR.

The results of the first experiment are depicted below in Table 6, which demonstrate that neither the surface of device itself nor the act of gyrating the mixing bead results in detectable nucleic acid loss or damage.

TABLE 6

| | Average of All Middle Aliquot $C_q$s | Standard Deviation of All Middle Aliquot $C_q$s |
|---|---|---|
| 2,060 rpm; alternating | 25.31 | 0.167 |
| No mixing | 25.44 | 0.223 |
| Positive control | 24.97 | 0.611 |

Example 6: Heat Staking

One experiment was performed to demonstrate the effectiveness of heat staking the apparatus, as described with regard to FIGS. 2E and 2F.

A test coupon was constructed, consisting of five wells, each connected to its own pneumatic compartment. The volumes of the wells (including the channels leading into the wells from the common line and the pneumatic conduit leading to the air chamber from the assay chamber) were 5.28 mm$^3$, 7.56 mm$^3$, 13.12 mm$^3$, 5.32 mm$^3$, and 9.96 mm$^3$, respectively. The volumes of the air chambers were 9.24 mm$^3$, 13.22 mm$^3$, 22.96 mm$^3$, 9.29 mm$^3$ and 17.43 mm$^3$, respectively. Water was filled into the sample coupon at a ramped pressure of 9.2 and 10 psi. The assay chambers filled evenly, and without significant bubbles caused by the filling process itself. At 9.2 psi, the wells were all substantially filled and at 10 psi, the wells were completely filled and the fluid extended into the pneumatic conduit connecting the wells to the air chambers. Therefore, a pressure in between the two (for instance 9.6 psi) was assumed to be ideal for complete filling.

After heat staking, the fluidic pathways hold pressure on both sides; air and water (to 10 psig). Furthermore, the fluidic pathways still hold pressure 10 days after heat staking (as observed by doming of pressurized wells and no liquid leakage.)

Example 7: Amplification and Detection

One experiment was performed to demonstrate that after heat staking the fluidic pathways described with regard to FIGS. 1-7, heating the fluidic pathways does not induce significant bubble formation within the sample chamber. A test coupon was constructed, consisting of five wells, as described in Example 6.

Isothermal Amplification Buffer (New England Biolabs) supplemented with $MgCl_2$, dNTPs, LAMP primers, FAM-molecular beacon probe, Bst 2 polymerase (New England Biolabs), and RTx Warmstart (reverse transcriptase; New England Biolabs), and 100,000 copies of CT 23S DNA (as template) was filled into the sample coupon with pressure ramping to 13 psi. The coupon was then heat staked and heated to 64° C. Very small bubbles formed in some assay chambers during the first few minutes at elevated temperature. Over the course of 30 minutes, these tiny bubbles were stable and did not interfere with amplification or image processing. Amplification within each of the five wells was visually detectable within 9-15 minutes of exposure to 64° C.

Reference Number List

| Item | Last 2 Digits |
| --- | --- |
| apparatus | 00 |
| common fluid source | 01 |
| monolithic substrate | 02 |
| heat stake | 03 |
| independent fluidic pathway | 10 |
| sample chamber | 20 |
| assay chamber | 21 |
| entry conduit | 22 |
| entry conduit terminus | 23 |
| pneumatic compartment | 30 |
| air chamber | 31 |
| pneumatic conduit | 32 |
| pneumatic compartment terminus | 33 |
| double tapered chamber | 40 |
| tapered inlet | 41 |
| tapered outlet | 42 |
| double tapered chamber center point | 43 |
| first curved boundary | 44 |
| second curved boundary | 45 |
| first curved boundary midpoint | 46 |
| second curved boundary midpoint | 47 |
| largest dimension | 48 |
| air | 50 |
| fluid sample | 60 |
| meniscus | 61 |
| leading front | 62 |
| plug | 70 |
| plug body | 71 |
| plug cap | 72 |
| plug cap flange | 73 |
| plug cap internal cavity | 74 |
| dried reagents | 75 |
| magnetic mixing element | 81 |
| exterior magnet | 82 |
| motor | 83 |
| heated element | 84 |

What is claimed is:

1. An apparatus, comprising:
(a) a common fluid source;
(b) a plurality of independent, continuous fluidic pathways, each independent, continuous fluidic pathway comprising:
(i) a sample chamber connected to the common fluid source, said sample chamber having a fluid volume and comprising an assay chamber and an entry conduit, wherein the assay chamber has an assay chamber volume, and wherein the entry conduit connects the common fluid source to the assay chamber; and
(ii) a pneumatic compartment connected to the sample chamber, said pneumatic compartment having a pneumatic volume; and
(c) a first film adhered to a surface of at least a portion of the apparatus, wherein the first film forms one wall of the entry conduit of each fluidic pathway; and
(d) a second film adhered to the first film, wherein the second film has a higher melting temperature than the first film,
wherein, excluding the connection between the sample chamber and the common fluid source, each fluidic pathway is a closed system, and wherein a ratio of the fluid volume to the pneumatic volume is substantially equivalent for each fluidic pathway of the plurality of fluidic pathways.

2. The apparatus of claim 1, wherein the fluid volume of a first fluidic pathway of the plurality of fluidic pathways is greater than the fluid volume of a second fluidic pathway of the plurality of fluidic pathways.

3. The apparatus of claim 1, wherein the pneumatic compartment comprises an air chamber and a pneumatic conduit, wherein the pneumatic conduit connects the sample chamber to the air chamber.

4. The apparatus of claim 1, wherein the assay chamber comprises:
a double tapered chamber, the double tapered chamber comprising:
a tapered inlet in fluidic communication with a terminus of the entry conduit of the fluidic pathway;
a tapered outlet in fluidic communication with a terminus of the pneumatic compartment, wherein the tapered inlet and the tapered outlet are separated by a largest dimension of the assay chamber volume; and
two curved boundaries, each curved boundary extending from the tapered inlet to the tapered outlet, the two curved boundaries together enclosing the assay chamber volume, wherein each curved boundary comprises a midpoint, and wherein a distance between the two curved boundaries decreases as the boundaries curve from the midpoint toward the tapered inlet and from the midpoint toward the tapered outlet.

5. The apparatus of claim 4, wherein the two curved boundaries of the double tapered chamber are concave with regard to a center point of the assay chamber volume.

6. The apparatus of claim 4, wherein the double tapered chamber is monolithic.

7. The apparatus of claim 1, wherein the assay chamber comprises a first bounding surface formed in a monolithic substrate and a second bounding surface formed by a plug, the plug comprising a body and a cap, the body protruding into the monolithic substrate at a depth, wherein the cap of the plug forms the second bounding surface of the assay chamber.

8. The apparatus of claim 7, wherein the assay chamber comprises a third bounding surface formed by a film, wherein the first bounding surface, second bounding surface, and third bounding surface together enclose the assay chamber volume.

9. The apparatus of claim 7, wherein an internal cavity formed in the cap of the plug contains one or more dried reagents.

10. The apparatus of claims 7, wherein the assay chamber volume depends at least in part on the depth at which the body of the plug protrudes into the monolithic substrate of the assay chamber.

11. The apparatus of claim 7, wherein the plug is transparent.

12. The apparatus of claim 1, wherein the assay chamber volume is between 1 µL and 35 µL.

13. The apparatus of claim 1, further comprising a magnetic mixing element located within the assay chamber of each fluidic pathway, wherein the magnetic mixing element is capable of gyration.

14. The apparatus of claim 13, wherein gyration of the magnetic mixing element is induced by rotation of a magnet exterior to the assay chamber.

15. A method of simultaneously filling a plurality of sample chambers, the method comprising:
providing an apparatus according to claim 1, wherein the common fluid source contains a fluid sample and each independent, continuous fluidic pathway contains a gas; and
applying a supply pressure to the fluid sample in the common fluid source whereby the fluid sample is forced into the sample chamber of each fluidic pathway via the entry conduit, whereupon transmitting the fluid sample into the sample chamber compresses the gas within the fluidic pathway toward the pneumatic compartment of the fluidic pathway, thereby increasing internal pressure in the pneumatic compartment, wherein when the internal pressure in the pneumatic compartment equals the supply pressure, the fluid sample stops flowing from the common fluid source into the fluidic pathway.

16. The method of claim 15, wherein the supply pressure is applied at a constant pressure.

17. The method of claim 15, wherein the supply pressure is applied ramping from a lower pressure to a higher pressure.

18. The method of claim 15, wherein a fluid volume of a sample chamber of a first fluidic pathway of the plurality of fluidic pathways is greater than a fluid volume of a sample chamber of a second fluidic pathway of the plurality of fluidic pathways, and wherein the sample chamber of the first fluidic pathway and the sample chamber of the second fluidic pathway fill at a substantially proportional rate.

19. The method of claim 15, wherein the fluid sample travels to the plurality of sample chambers via the entry conduits against a gravitational force.

20. The method of claim 15, wherein at least two sample chambers of the plurality of sample chambers differ in volume, and wherein a rate of flow from the common fluid source into each sample chamber of the plurality of sample chambers is proportional to a fluid volume of the sample chamber, thereby enabling simultaneous filling of the plurality of sample chambers.

21. The method of claim 15, wherein the assay chamber of each sample chamber comprises:

a double tapered chamber, the double tapered chamber comprising:
a tapered inlet in fluidic communication with a terminus of the entry conduit of the fluidic pathway;
a tapered outlet in fluidic communication with a terminus of the pneumatic compartment, wherein the tapered inlet and the tapered outlet are separated by a largest dimension of the assay chamber volume; and
two curved boundaries, each curved boundary extending from the tapered inlet to the tapered outlet, the two curved boundaries together enclosing the assay chamber volume, wherein each curved boundary comprises a midpoint, and wherein a distance between the two curved boundaries decreases as the boundaries curve from the midpoint toward the tapered inlet and from the midpoint toward the tapered outlet.

22. The method of claim 21, wherein the two curved boundaries of the double tapered chamber slow a rate of fluid advance at a leading front of a meniscus of the fluid sample, such that when the fluid sample reaches the tapered outlet, the meniscus of the fluid sample is substantially symmetric with respect to the largest dimension of the assay chamber, thereby minimizing the trapping of bubbles within the assay chamber during filling.

23. The method of claim 15, further comprising sealing the entry conduit of each fluidic pathway of the plurality of fluidic pathways when the fluid sample stops flowing from the common fluid source into the fluidic pathway.

24. The method of claim 23, wherein the step of sealing is performed by heat staking.

25. An apparatus for rehydrating a dried reagent, the apparatus comprising:
an assay chamber comprising a first bounding surface formed in a monolithic substrate and a second bounding surface formed by a plug, the plug comprising a body and a cap, the body protruding into the monolithic substrate at a depth, wherein the cap of the plug forms the second bounding surface of the assay chamber, thereby enclosing a volume of the assay chamber;
one or more dried reagents contained in an internal cavity formed in the cap of the plug; and
a magnetic mixing element configured to induce gyration within the assay chamber volume.

26. The apparatus of claim 25, wherein the assay chamber comprises a third bounding surface comprised of a film, wherein the first bounding surface, second bounding surface and third bounding surface together enclose the assay chamber volume.

27. A method of solubilizing a dried reagent, the method comprising:
providing an apparatus according to claim 25;
filling the assay chamber with a fluid;
inducing gyration of the magnetic mixing element by rotation of a magnet exterior to the assay chamber, thereby solubilizing the reagent in the fluid.

* * * * *